(12) United States Patent
Muragaki et al.

(10) Patent No.: US 6,872,858 B2
(45) Date of Patent: Mar. 29, 2005

(54) DIPHENOL AND PROCESS FOR PRODUCING THE SAME

(75) Inventors: Kouji Muragaki, Wakayama (JP); Tadashi Hiramine, Wakayama (JP); Hiroyasu Ohno, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/467,187

(22) PCT Filed: Feb. 7, 2002

(86) PCT No.: PCT/JP02/01055
§ 371 (c)(1),
(2), (4) Date: Aug. 5, 2003

(87) PCT Pub. No.: WO02/062736
PCT Pub. Date: Aug. 15, 2002

(65) Prior Publication Data
US 2004/0049086 A1 Mar. 11, 2004

(30) Foreign Application Priority Data

| | | |
|---|---|---|
| Feb. 8, 2001 | (JP) | 2001-031959 |
| Feb. 8, 2001 | (JP) | 2001-031960 |
| Feb. 8, 2001 | (JP) | 2001-031961 |
| Apr. 27, 2001 | (JP) | 2001-133677 |
| Jun. 25, 2001 | (JP) | 2001-191006 |
| Nov. 15, 2001 | (JP) | 2001-349824 |
| Feb. 1, 2002 | (JP) | 2002-025452 |

(51) Int. Cl.$^7$ ............................................. C07L 39/12
(52) U.S. Cl. ........................................ 568/718; 568/721
(58) Field of Search .................................. 568/718, 721

(56) References Cited

U.S. PATENT DOCUMENTS

| | | | | |
|---|---|---|---|---|
| 3,408,407 A | * | 10/1968 | Cotter et al. ................. | 568/721 |
| 3,461,098 A | * | 8/1969 | Apel et al. ................... | 528/196 |
| 5,366,843 A | * | 11/1994 | Jeffries, III ................. | 430/165 |

FOREIGN PATENT DOCUMENTS

JP           01168632 A    *   7/1989           C07C/39/15

* cited by examiner

Primary Examiner—Michael L. Shippen
(74) Attorney, Agent, or Firm—Merchant & Gould P.C.

(57) ABSTRACT

The invention provides a diphenol represented by the general formula (I)

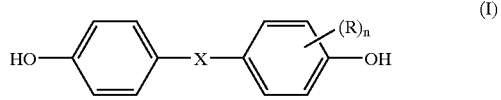

wherein X is a divalent cyclic hydrocarbon group selected from 1-cyclohexene-1,4-ylene group, 1,4-cyclohexylene group and p-phenylene group, R is an alkyl group of 1–4 carbon atoms, n is 0 or an integer of 1–3 when X is 1-cyclohexene-1,4-ylene group and an integer of 1–3 when X is 1,4-cyclohexylene group or p-phenylene group. The invention further provides a process for the production of the same.

5 Claims, No Drawings

DIPHENOL AND PROCESS FOR PRODUCING THE SAME

TECHNICAL FIELD

The invention relates to new diphenols which have two phenolic nuclei (hydroxyphenyl groups) bonded to a divalent cyclic hydrocarbon group and a process for production of the same. More particularly, the invention relates to new diphenols in which neither phenolic nuclei have a substituent or only one of the phenolic nuclei has a lower alkyl group as a substituent, in particular, 1,4-bis(4-hydroxyphenyl)-1-cyclohexenes, 4-(4'-(4"-hydroxyphenyl)cyclohexyl)-1-hydroxybenzenes or 4,4"-dihydroxy-p-terphenyls, and process for production of these new diphenols.

BACKGROUND ART 4,4"-dihydroxy-p-terphenyls are useful not only as intermediate raw materials for production of various kinds of resins such as liquid crystalline polyesters, polycarbonates, polyurethanes, polyimides or polyamides but also as raw materials for various kinds of liquid crystal materials exemplified by liquid crystal display elements, raw materials for photoresists for use in the production of semiconductors, or as raw materials for organic electroluminescence elements.

1,4-bis(4-hydroxyphenyl)-1-cyclohexenes are themselves useful as intermediate raw materials for production of various kinds of resins similarly to 4,4"-dihydroxy-p-terphenyls as mentioned above. They are also useful as intermediate raw materials for the production of a variety of organic compounds or liquid crystal materials. For example, the dehydrogenation of the cyclohexene portion of the molecule of 1,4-bis(4-hydroxyphenyl)-1-cyclohexenes provides 4,4"-dihydroxy-p-terphenyls as above mentioned.

In turn, 4-(4'-(4"-hydroxyphenyl)cyclohexyl)-1-hydroxybenzenes are themselves useful as intermediate raw materials for production of various kinds of resins or liquid crystal materials similarly to 4,4"-dihydroxy-p-terphenyls as mentioned above. In addition, they provide 4,4"-dihydroxy-p-terphenyls as above mentioned when they are dehydrogenated.

Hitherto known dihydroxyterphenyls such as 4,4"-dihydroxy-p-terphenyl which has a symmetrical molecular structure or 4,4"-dihydroxy-3-phenyl-p-terphenyl which has an unsymmetrical molecular structure find problems, for example, that they have only limited solubility in solvents when they are used as raw materials for production of synthetic resins or photoresists. Accordingly, there is a strong demand for novel 4,4"-dihydroxy-p-terphenyls which have improved solubility in solvents so as to be more effectively made use of in a variety of fields as raw materials for production of synthetic resins or photoresists.

According to a known process for the production of 4,4"-dihydroxy-p-terphenyls, 4-methoxy-4'-bromobiphenyl is Grignard-coupled with 4-methoxy-3-phenylmagnesium bromide followed by demethylation, as described in, for example, Japanese Patent Laid-Open No. 2-212449. However, this process uses special raw materials and in addition, it resorts to Grignard reaction so that it costs a great deal and it is difficult to work the process in an industrial manner.

A further process is also known in which 1,1,4,4-tetrakis (4-hydroxyphenyl)cyclohexane is first produced by using 1,4-cyclohexanedione and a phenol, and it is then thermally decomposed and dehydrogenated, as described in Japanese Patent Laid-Open No. 1-168632. However, this process gives 1,1,4,4-tetrakis(4-hydroxyphenyl)cyclohexane or an intermediate raw material only in low yields, and hence the production of the intermediate raw material is costly. The process also needs to carry out the decomposition reaction at a high temperature under a high pressure in an autoclave. Furthermore, the thermal decomposition and dehydrogenation of 1,1,4,4-tetrakis(4-hydroxy-phenyl)cyclohexane fails to provide desired products, that is, 4,4"-dihydroxy-p-terphenyls having a substituent only on one of the terminal 4-hydroxyphenyl groups of the molecule and thus having an unsymmetrical molecular structure.

On the other hand, some of 1,4-bis(4-hydroxyphenyl)-1-cyclohexenes having substituents such as a carboxymethyl group and a naphthyl group (CAS registration number 101789-46-2) or a phenyl group (CAS registration number 202266-25-9) are mentioned in the Chemical Abstracts. However, 1,4-bis-(4-hydroxyphenyl)-1-cyclohexenes having no substituents on either phenolic nuclei or lower alkyl groups only on one of the phenolic nuclei of the molecule are not known.

With regard to 4-(4'-(4"-hydroxyphenyl)cyclohexyl)-1-hydroxybenzenes, 1,4-bis(4-hydroxyphenyl)cyclohexane which is symmetrical with respect to the cyclohexyl group is described in Japanese Patent Laid-Open No. 1-168634 or U.S. Pat. No. 3,408,407. However, 4-(4'-(4"-hydroxyphenyl)cyclohexyl)-1-hydroxybenzenes having lower alkyl groups as substituents only one of the phenolic nuclei are not known, and much less about their trans- and cis-isomers.

Under these circumstances of novel diphenols which have two phenolic nuclei attached to a divalent cyclic hydrocarbon group, the present invention has been completed. Therefore, it is an object of the invention to provide, in particular, novel 4,4"-dihydroxy-p-terphenyls which have lower alkyl groups only on one of the terminal phenolic nuclei of the molecule and hence have an unsymmetrical molecular structure so that they have improved solubility in various organic solvents.

It is a further object of the invention to provide not only novel 1,4-bis(4-hydroxyphenyl)-1-cyclohexenes which have lower alkyl groups only on one of the phenolic nuclei as substituents and are useful as raw materials for production of such 4,4"-dihydroxy-p-terphenyls as mentioned above, but also novel 1,4-bis(4-hydroxyphenyl)-1-cyclohexenes which have no lower alkyl groups on either phenolic nuclei.

It is still an object of the invention to provide 4-(4'-(4"-hydroxyphenyl)cyclohexyl)-1-hydroxybenzenes which have lower alkyl groups on only one of the phenolic nuclei as substituents and which are themselves useful as diols which have hydroxyl group at both the terminals of the molecule for production of, for instance, synthetic resins such as polyesters, polycarbonates or polyurethanes, as well as useful as intermediate raw materials for production of 4,4"-dihydroxy-p-terphenyls.

It is a still further object of the invention to provide trans isomers of the above-mentioned compounds, that is, 4-(trans-4'-(4"-hydroxyphenyl)cyclohexyl)-1-hydroxybenzenes and cis isomers, that is, 4-(cis-4'-(4"-hydroxyphenyl)cyclohexyl)-1-hydroxybenzenes.

In addition, it is also an object of the invention to provide a process for production of a variety of 4,4"-dihydroxy-p-terphenyls in high yield and in high purity under industrially feasible reaction conditions by using raw materials that are industrially readily available.

SUMMARY OF THE INVENTION

According to the invention, there is provided a diphenol represented by the general formula (I)

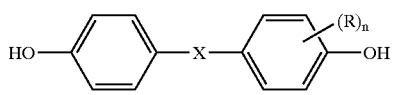

wherein X is a divalent cyclic hydrocarbon group selected from 1-cyclohexene-1,4-ylene, 1,4-cyclohexylene and p-phenylene group, R is an alkyl group of 1–4 carbon atoms, n is 0 or an integer of 1–3 when X is 1-cyclohexene-1,4-ylene group and an integer of 1–3 when X is 1,4-cyclohexylene group or p-phenylene group.

Further according to the invention, there is provided a process for production of a 4,4"-dihydroxy-p-terphenyl represented by the general formula (Ic')

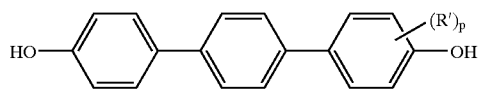

wherein R' is independently an alkyl, an alkoxyl or an haloalkoxyl group each of 1–12 carbon atoms, a cycloalkyl, a cycloalkoxyl or a halocycloalkoxyl group each of 5 or 6 carbon atoms, a phenyl or a hydroxyl group, p is 0 or an integer of 1–3, which comprises thermally decomposing a hydroxyphenyl substituted cyclohexylidene bisphenol represented by the general formula (II')

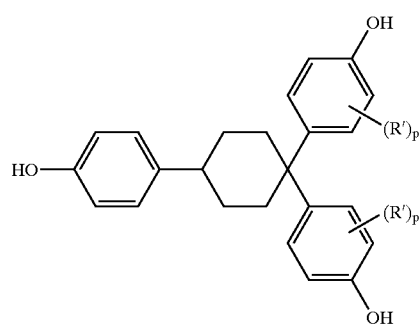

wherein R' and p are the same as mentioned above, and then subjecting the resulting reaction mixture to dehydrogenation reaction.

EMBODIMENTS OF THE INVENTION

The diphenol of the invention is represented by the general formula (I)

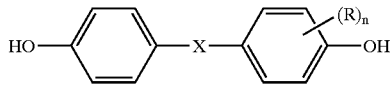

wherein X is a divalent cyclic hydrocarbon group selected from 1-cyclohexene-1,4-ylene, 1,4-cyclohexylene and p-phenylene group, R is an alkyl group of 1–4 carbon atoms, n is 0 or an integer of 1–3 when X is 1-cyclohexene-1,4-ylene group and an integer of 1–3 when X is 1,4-cyclohexylene or p-phenylene group.

In the diphenol represented by the above-mentioned general formula (I), the alkyl group R is an alkyl group of 1–4 carbon atoms such as methyl, ethyl, propyl or butyl group, and the propyl group or butyl group may linear or branched.

The first one of the diphenols represented by the general formula (I) according to the invention is 1,4-bis(4-hydroxyphenyl)-1-cyclohexene which is represented by the general formula (Ia)

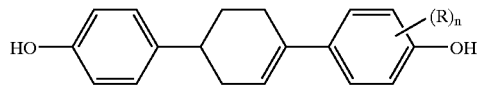

wherein R is an alkyl group of 1–4 carbon atoms and n is 0 or an integer of 1–3.

Examples of the 1,4-bis(4-hydroxyphenyl)-1-cyclohexene having the general formula (Ia) includes, for example:

1,4-bis(4-hydroxyphenyl)-1-cyclohexene,
1-(3-methyl-4-hydroxyphenyl)-4-(4-hydroxyphenyl)-1-cyclohexene,
1-(2-methyl-4-hydroxyphenyl)-4-(4-hydroxyphenyl)-1-cyclohexene,
1-(3-ethyl-4-hydroxyphenyl)-4-(4-hydroxyphenyl)-1-cyclohexene,
1-(2-ethyl-4-hydroxyphenyl)-4-(4-hydroxyphenyl)-1-cyclohexene,
1-(3-n-propyl-4-hydroxyphenyl)-4-(4-hydroxyphenyl)-1-cyclohexene,
1-(2-n-propyl-4-hydroxyphenyl)-4-(4-hydroxyphenyl)-1-cyclohexene,
1-(3-isopropyl-4-hydroxyphenyl)-4-(4-hydroxyphenyl)-1-cyclohexene,
1-(2-isopropyl-4-hydroxyphenyl)-4-(4-hydroxyphenyl)-1-cyclohexene,
1-(3-n-butyl-4-hydroxyphenyl)-4-(4-hydroxyphenyl)-1-cyclohexene,
1-(2-n-butyl-4-hydroxyphenyl)-4-(4-hydroxyphenyl)-1-cyclohexene,
1-(3-isobutyl-4-hydroxyphenyl)-4-(4-hydroxyphenyl)-1-cyclohexene,
1-(2-isobutyl-4-hydroxyphenyl)-4-(4-hydroxyphenyl)-1-cyclohexene,
1-(3-s-butyl-4-hydroxyphenyl)-4-(4-hydroxyphenyl)-1-cyclohexene,
1-(2-s-butyl-4-hydroxyphenyl)-4-(4-hydroxyphenyl)-1-cyclohexene,
1-(3-t-butyl-4-hydroxyphenyl)-4-(4-hydroxyphenyl)-1-cyclohexene,
1-(2-t-butyl-4-hydroxyphenyl)-4-(4-hydroxyphenyl)-1-cyclohexene,
1-(3,6-dimethyl-4-hydroxyphenyl)-4-(4-hydroxyphenyl)-1-cyclohexene,
1-(3,5-dimethyl-4-hydroxyphenyl)-4-(4-hydroxyphenyl)-1-cyclohexene,
1-(2,3,6-trimethyl-4-hydroxyphenyl)-4-(4-hydroxyphenyl)-1-cyclohexene,
1-(2,3,5-trimethyl-4-hydroxyphenyl)-4-(4-hydroxyphenyl)-1-cyclohexene,
1-(3-isopropyl-6-methyl-4-hydroxyphenyl)-4-(4-hydroxyphenyl)-1-cyclohexene,
1-(3-isopropyl-5-methyl-4-hydroxyphenyl)-4-(4-hydroxyphenyl)-1-cyclohexene,
1-(3-t-butyl-6-methyl-4-hydroxyphenyl)-4-(4-hydroxyphenyl)-1-cyclohexene,
1-(3-t-butyl-5-methyl-4-hydroxyphenyl)-4-(4-hydroxyphenyl)-1-cyclohexene,
1-(3,5-di-t-butyl-5-methyl-4-hydroxyphenyl)-4-(4-hydroxyphenyl)-1-cyclohexene, and 1-(3,5-diisopropyl-4-hydroxyphenyl)-4-(4-hydroxyphenyl)-1-cyclohexane.

Among these are preferred, in particular, 1,4-bis(4-hydroxyphenyl)-1-cyclohexene,
1-(3-methyl-4-hydroxyphenyl)-4-(4-hydroxyphenyl)-1-cyclohexene, and
1-(3,5-dimethyl-4-hydroxyphenyl)-4-(4-hydroxyphenyl)-1-cyclohexane.

The 1,4-bis(4-hydroxyphenyl)-1-cyclohexene represented by the general formula (Ia) according to the invention is obtained by, for example, thermally decomposing a hydroxyphenyl substituted cyclohexylidene bisphenols represented by the general formula (II)

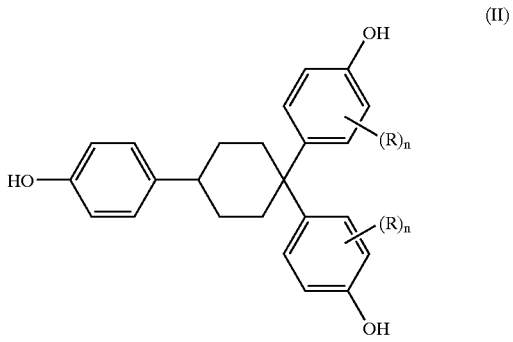

wherein R is an alkyl group of 1–4 carbon atoms and n is 0 or an integer of 1–4, preferably in the presence of an alkali catalyst.

The hydroxyphenyl substituted cyclohexylidene bisphenol represented by the general formula (II) or the starting material for the production of 1,4-bis(4-hydroxyphenyl)-1-cyclohexene of the invention is already known, as described hereinafter, and there are mentioned as examples thereof:

1-(4-hydroxyphenyl)-4,4-bis(4-hydroxyphenyl) cyclohexane,
1-(4-hydroxyphenyl)-4,4-bis(3-methyl-4-hydroxyphenyl)-cyclohexane,
1-(4-hydroxyphenyl)-4,4-bis(2-methyl-4-hydroxyphenyl)-cyclohexane,
1-(4-hydroxyphenyl)-4,4-bis(3,5-dimethyl-4-hydroxyphenyl)-cyclohexane,
1-(4-hydroxyphenyl)-4,4-bis(3,6-dimethyl-4-hydroxyphenyl)-cyclohexane,
1-(4-hydroxyphenyl)-4,4-bis(2,3,5-trimethyl-4-hydroxyphenyl)-cyclohexane,
1-(4-hydroxyphenyl)-4,4-bis(2,3,6-trimethyl-4-hydroxyphenyl)-cyclohexane,
1-(4-hydroxyphenyl)-4,4-bis(3-ethyl-4-hydroxyphenyl)-cyclohexane,
1-(4-hydroxyphenyl)-4,4-bis(2-ethyl-4-hydroxyphenyl)-cyclohexane,
1-(4-hydroxyphenyl)-4,4-bis(3-isopropyl-4-hydroxyphenyl)-cyclohexane,
1-(4-hydroxyphenyl)-4,4-bis(2-isopropyl-4-hydroxyphenyl)-cyclohexane,
1-(4-hydroxyphenyl)-4,4-bis(3-isobutyl-4-hydroxyphenyl)-cyclohexane,
1-(4-hydroxyphenyl)-4,4-bis(2-isobutyl-4-hydroxyphenyl)-cyclohexane,
1-(4-hydroxyphenyl)-4,4-bis(3-s-butyl-4-hydroxyphenyl)-cyclohexane,
1-(4-hydroxyphenyl)-4,4-bis(2-s-butyl-4-hydroxyphenyl)-cyclohexane,
1-(4-hydroxyphenyl)-4,4-bis(3-isopropyl-6-methyl-4-hydroxyphenyl)cyclohexane,
1-(4-hydroxyphenyl)-4,4-bis(3-isopropyl-5-methyl-4-hydroxyphenyl)cyclohexane,
1-(4-hydroxyphenyl)-4,4-bis (3-t-butyl-6-methyl-4-hydroxyphenyl)cyclohexane, and
1-(4-hydroxyphenyl)-4,4-bis(3,5-di-t-butyl-4-hydroxyphenyl)cyclohexane.

The thermal decomposition of the hydroxyphenyl substituted cyclohexylidene bisphenol may be carried out in the absence of a catalyst, but it is preferred that it is carried out in the presence of an alkali catalyst. The alkali catalyst usable includes, for example, alkali metal hydroxides such as sodium hydroxide, potassium hydroxide or lithium hydroxide, alkali metal carbonates such as sodium carbonate or potassium carbonate, alkali metal hydrogencarbonates such as sodium hydrogencarbonate or potassium hydrogencarbonate, alkali metal phenoxides such as sodium phenoxide or potassium phenoxide, and alkaline earth metal hydroxides such as magnesium hydroxide, calcium hydroxide or barium hydroxide. Although the alkali catalyst usable is not specifically limited to those above exemplified, but among these are preferred in particular sodium hydroxide or potassium hydroxide.

When an alkali catalyst is used, the amount thereof is usually in the range of 0.01–30 parts by weight, preferably in the range of 0.1–10 parts by weight, in relation to 100 parts by weight of the hydroxyphenyl substituted cyclohexylidene bisphenol used. The catalyst may be used in any form, but it is preferred that it is used in the form of aqueous solution having a concentration of 10–50% by weight so that it is easy to treat.

Furthermore, the thermal decomposition of the hydroxyphenyl substituted cyclohexylidene bisphenol is carried out preferably in the presence of a solvent so that the reaction proceeds stably in liquid phase at the thermal decomposition temperature since the starting material, i.e., the hydroxyphenyl substituted cyclohexylidene bisphenol and/or the reaction product, i.e., 1,4-bis-(4-hydroxyphenyl)-1-cyclohexene has a high melting point, as well as the reaction product is prevented from thermal polymerization under the reaction temperature.

The reaction solvent usable includes, for example, polyethylene glycols such as triethylene glycol, tetraethylene glycol, or polypropylene glycols such as tripropylene glycol or tetrapropylene glycol, polyhydric alcohols such as glycerin. Further examples of solvents usable are commercially available organic heat transfer media "Thermes" (available from Nippon Steel Chemical Co., Ltd.) or "SK-OIL" (available from Soken Chemical & Engineering Co., Ltd.). However, the reaction solvent usable is not limited to those above exemplified.

The reaction solvent is used in an amount usually of 10–150 parts by weight, preferably in an amount of 30–100 parts by weight, in relation to 100 parts by weight of the hydroxyphenyl substituted cyclohexylidene bisphenol used.

The thermal decomposition of the hydroxyphenyl substituted cyclohexylidene bisphenol is carried out usually at a temperature of 150–300° C., preferably at a temperature of 180–250° C. When the thermal decomposition temperature is too low, the reaction rate is too slow, while when the thermal decomposition temperature is too high, the thermal decomposition reason is accompanied by undesirable side reactions. The reaction pressure under which the thermal decomposition of the hydroxyphenyl substituted cyclohexylidene bisphenol is carried out is not limited specifically, however, the thermal decomposition is carried out usually under normal pressure or reduced pressure, for example, under a pressure in the range of 1–760 mmHg gage, preferably under a pressure in the range of 30–50 mmHg gage.

Under the reaction conditions as mentioned above, the thermal decomposition of the hydroxyphenyl substituted cyclohexylidene bisphenol is completed usually in 1–6 hours. For example, the end point of the thermal decomposition reaction is reached when the distillation of the alkyl phenols generated by the thermal decomposition reaction has ceased.

According to a preferred embodiment of the invention, the thermal decomposition of the hydroxyphenyl substituted cyclohexylidene bisphenol is carried out by placing a starting material, a hydroxyphenyl substituted cyclohexylidene bisphenol, an alkali catalyst and a solvent such as tetraethylene glycol in a reaction vessel and stirring the resulting mixture at a temperature of 190–220° C. under a pressure of 30–50 mmHg gauge for a period of 3–6 hours while distilling the alkyl phenol generated by the thermal decomposition reaction out of the reaction vessel. In this way, the thermal decomposition of the hydroxyphenyl substituted cyclohexylidene bisphenol provides the 1,4-bis(4-hydroxyphenyl)-1-cyclohexenes of the invention usually in yields of about 90%.

The hydrogenation of 1,4-bis(4-hydroxyphenyl)-1-cyclohexene which has an alkyl group on one of the phenolic nuclei among the 1,4-bis(4-hydroxyphenyl)-1-cyclohexenes thus obtained provides the 4-(4'-(4"-hydroxyphenyl)cyclohexyl)-1-hydroxybenzene of the invention. That is, the second one of the diphenols of the invention represented by the general formula (I) is 4-(4'-(4"-hydroxyphenyl)cyclohexyl)-1-hydroxybenzene having the general formula (Ib)

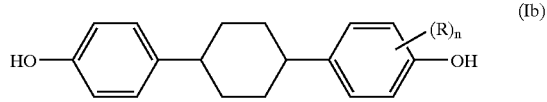

(Ib)

wherein R is an alkyl group of 1–4 carbon atoms and n is an integer of 1–3.

Accordingly, there are mentioned as examples of 4-(4'-(4"-hydroxyphenyl)cyclohexyl)-1-hydroxybenzene of the invention, for example:

4-(4'-(4"-hydroxyphenyl)cyclohexyl)-2-methyl 1-hydroxybenzene,
4-(4'-(4"-hydroxyphenyl)cyclohexyl)-3-methyl 1-hydroxybenzene,
4-(4'-(4"-hydroxyphenyl)cyclohexyl)-2,6-dimethyl-1-hydroxybenzene,
4-(4'-(4"-hydroxyphenyl)cyclohexyl)-2,3-dimethyl-1-hydroxybenzene,
4-(4'-(4"-hydroxyphenyl)cyclohexyl)-2,5-dimethyl-1-hydroxybenzene,
4-(4'-(4"-hydroxyphenyl)cyclohexyl)-2,3,5-trimethyl-1-hydroxybenzene,
4-(4'-(4"-hydroxyphenyl)cyclohexyl)-2,3,6-trimethyl-1-hydroxybenzene,
4-(4'-(4"-hydroxyphenyl)cyclohexyl)-2-ethyl-1-hydroxybenzene,
4-(4'-(4"-hydroxyphenyl)cyclohexyl)-3-ethyl-1-hydroxybenzene,
4-(4'-(4"-hydroxyphenyl)cyclohexyl)-2-isopropyl-1-hydroxybenzene,
4-(4'-(4"-hydroxyphenyl)cyclohexyl)-3-isopropyl-1-hydroxybenzene,
4-(4'-(4"-hydroxyphenyl)cyclohexyl)-2-n-propyl-1-hydroxybenzene,
4-(4'-(4"-hydroxyphenyl)cyclohexyl)-3-n-propyl-1-hydroxybenzene,
4-(4'-(4"-hydroxyphenyl)cyclohexyl)-2-n-butyl-1-hydroxybenzene,
4-(4'-(4"-hydroxyphenyl)cyclohexyl)-3-n-butyl-1-hydroxybenzene,
4-(4'-(4"-hydroxyphenyl)cyclohexyl)-2-t-butyl-1-hydroxybenzene,
4-(4'-(4"-hydroxyphenyl)cyclohexyl)-3-t-butyl-1-hydroxybenzene,
4-(4'-(4"-hydroxyphenyl)cyclohexyl)-2,6-diethyl-1-hydroxybenzene,
4-(4'-(4"-hydroxyphenyl)cyclohexyl)-2,3-diethyl-1-hydroxybenzene,
4-(4'-(4"-hydroxyphenyl)cyclohexyl)-2,5-diethyl-1-hydroxybenzene,
4-(4'-(4"-hydroxyphenyl)cyclohexyl)-2,3,5-triethyl-1-hydroxybenzene,
4-(4'-(4"-hydroxyphenyl)cyclohexyl)-2,3,6-triethyl-1-hydroxybenzene,
4-(4'-(4"-hydroxyphenyl)cyclohexyl)-2,6-diisopropyl-1-hydroxybenzene,
4-(4'-(4"-hydroxyphenyl)cyclohexyl)-2,3-diisopropyl-1-hydroxybenzene
4-(4'-(4"-hydroxyphenyl)cyclohexyl)-2,5-diisopropyl-1-hydroxybenzene
4-(4'-(4"-hydroxyphenyl)cyclohexyl)-2,6-di-t-butyl-1-hydroxybenzene,
4-(4'-(4"-hydroxyphenyl)cyclohexyl)-2,3-di-t-butyl-1-hydroxybenzene
4-(4'-(4"-hydroxyphenyl)cyclohexyl)-2,5-di-t-butyl-1-hydroxybenzene
4-(4'-(4"-hydroxyphenyl)cyclohexyl)-2-methyl-6-isopropyl-1-hydroxybenzenes,
4-(4'-(4"-hydroxyphenyl)cyclohexyl)-2-t-butyl-5-methyl-1-hydroxybenzenes,
4-(4'-(4"-hydroxyphenyl)cyclohexyl)-2-methyl-6-t-butyl-1-hydroxybenzenes, and
4-(4'-(4"-hydroxyphenyl)cyclohexyl)-2,6-di-t-butyl-5-methyl-1-hydroxybenzene.

The 4-(4'-(4"-hydroxyphenyl)cyclohexyl)-1-hydroxybenzene of the invention is obtained by, for instance, hydrogenation of the cyclohexene ring of 1,4-bis(4-hydroxyphenyl)-1-cyclohexene represented by the general formula (Ia)

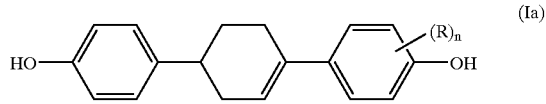

(Ia)

wherein R is an alkyl group of 1–4 carbon atoms and n is an integer of 1–3, in the presence of a hydrogenation catalyst.

The 1,4-bis(4-hydroxyphenyl)-1-cyclohexene as mentioned above is exemplified by those which have lower alkyl groups on one of the two phenolic nuclei among those which are exemplified hereinbefore.

In turn, the 1,4-bis(4-hydroxyphenyl)-1-cyclohexene represented by the general formula (Ia) is obtained by, for instance, thermally decomposing the hydroxyphenyl substituted cyclohexylidene bisphenol having the general formula (II)

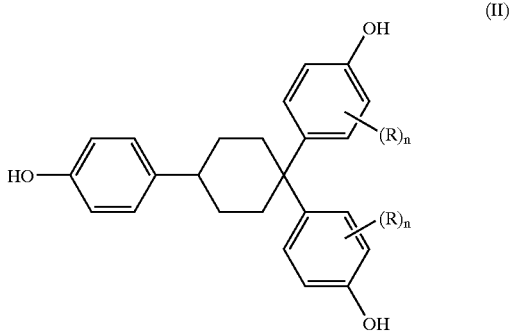

(II)

wherein R is an alkyl group of 1–4 carbon atoms and n is an integer of 1–3, preferably in the presence of an alkali catalyst.

The hydroxyphenyl substituted cyclohexylidene bisphenol as mentioned above is exemplified by those which have alkyl groups on the two phenolic nuclei among those which are exemplified hereinbefore.

Therefore, the 4-(4'-(4"-hydroxyphenyl)cyclohexyl)-1-hydroxybenzene of the invention is obtained by hydrogenation of the 1,4-bis(4-hydroxyphenyl)-1-cyclohexene according to a process among others.

According to further processes, the 4-(4'-(4"-hydroxyphenyl)cyclohexyl)-1-hydroxybenzene of the invention is obtained as follows. The hydroxyphenyl substituted cyclohexylidene bisphenol is thermally decomposed and when an alkali catalyst has been used in the thermal decomposition reaction, an acid is added to the resulting reaction mixture which contains 1,4-bis(4-hydroxyphenyl)-1-cyclohexene to neutralize the alkali catalyst, and then without purification operation such as crystallization or filtration of the thus treated reaction mixture, it is hydrogenated in the presence of a hydrogenation catalyst, thereby providing the 4-(4'-(4"-hydroxyphenyl)cyclohexyl)-1-hydroxybenzene of the invention.

When an alkali catalyst has not been used in the thermal decomposition reaction of the hydroxyphenyl substituted cyclohexylidene bisphenol, the resulting reaction mixture, with no purification operation such as crystallization or filtration applied thereto, is hydrogenated in the presence of a hydrogenation catalyst, thereby providing the 4-(4'-(4"-hydroxyphenyl)-cyclohexyl)-1-hydroxybenzene of the invention.

As mentioned as above, starting with 1,4-bis(4-hydroxyphenyl)-1-cyclohexene, the 4-(4'-(4"-hydroxyphenyl)cyclohexyl)-1-hydroxybenzene of the invention is obtained usually in yields of not less than 95%. On the other hand, starting with the hydroxyphenyl substituted cyclohexylidene bisphenol, the 4-(4'-(4"-hydroxyphenyl)cyclohexyl)-1-hydroxybenzene of the invention is obtained usually in yields of not less than 90%.

In order to obtain the 4-(4'-(4"-hydroxyphenyl)cyclohexyl)-1-hydroxybenzene of the invention by hydrogenation of 1,4-bis(4-hydroxyphenyl)-1-cyclohexene, more particularly, by hydrogenation of the cyclohexane ring of the 1,4-bis(4-hydroxyphenyl)-1-cyclohexene, the 1,4-bis(4-hydroxyphenyl)-1-cyclohexene is hydrogenated in the presence of a hydrogenation catalyst in a solvent at a temperature of 20–60° C.

As the hydrogenation catalyst, any known one may be suitably used. Therefore, it is exemplified by, for example, nickel catalysts such as Raney nickel or nickel supporting catalysts, cobalt catalysts such as Raney cobalt or cobalt supporting catalysts, copper catalysts such as Raney copper, palladium catalysts such as palladium oxide, palladium black or palladium/carbon catalyst, platinum catalysts such as platinum black or platinum/carbon catalyst, rhodium catalysts, chromium catalysts or copper-chromium catalysts. Among these exemplified, platinum group catalysts such as palladium group catalysts are preferred and in particular, palladium catalysts are most preferred.

The hydrogenation catalyst is used usually in an amount of 0.1–20 parts by weight, preferably in an amount of 0.2–10 parts by weight, in relation to 100 parts by weight of the starting material, 1,4-bis(4-hydroxyphenyl)-1-cyclohexene used.

The hydrogenation of the 1,4-bis(4-hydroxyphenyl)-1-cyclohexene is carried out preferably in an organic solvent. The solvent usable includes, for example, aliphatic saturated alcohols of not more than three carbon atoms such as methanol, ethanol or isopropanol, or aliphatic cyclic ethers such as tetrahydrofuran are preferably used from the reason that these solvents enhance the selectivity of reaction and in addition the reaction product of the thermal decomposition or 1,4-bis(4-hydroxyphenyl)-1-cyclohexene and the obtained product or 4-(4'-(4"-hydroxyphenyl)cyclohexyl)-1-hydroxybenzene are easy to dissolve in these solvents. The solvent is used alone or as a mixture of two or more of the above.

The solvent is used usually in an amount of 100–2000 parts by weight, preferably in an amount of 500–1000 parts by weight, in relation to 100 parts by weight of the starting material, 1,4-bis(4-hydroxyphenyl)-1-cyclohexene used, although depending upon the kind of individual 1,4-bis(4-hydroxyphenyl)-1-cyclohexene used or the kind of solvent used.

According to the invention, the use of the solvent in such an amount as mentioned above raises the conversion rate of 1,4-bis(4-hydroxyphenyl)-1-cyclohexene used as well as the selectivity of the desired 4-(4'-(4"-hydroxyphenyl)cyclohexyl)-1-hydroxybenzene, and hence makes it possible to obtain the desired 4-(4'-(4"-hydroxyphenyl)cyclohexyl)-1-hydroxybenzene in high yields.

It is preferred that the hydrogenation of 1,4-bis(4-hydroxyphenyl)-1-cyclohexene is carried out in a reactor inside of which has been replaced by an inert gas such as nitrogen gas or argon gas, and then by hydrogen gas. The amount of hydrogen gas supplied to the reaction vessel may be a theoretical amount that is necessary for the hydrogenation of the 1,4-bis(4-hydroxyphenyl)-1-cyclohexene to provide the desired 4-(4'-(4"-hydroxyphenyl)cyclohexyl)-1-hydroxybenzene.

The reaction temperature of hydrogenation of 1,4-bis(4-hydroxyphenyl)-1-cyclohexene is usually in the range of 0–100° C., preferably in the range of 20–60° C., while the hydrogen pressure in the reaction is usually in the range of 1–10 kg/cm$^2$ G, preferably in the range of 2–4 kg/cm$^2$ G. The reaction time is usually in the range of 0.1–10 hours, preferably in the range of 0.2–2 hours, although depending upon the reaction conditions employed.

The 4-(4'-(4"-hydroxyphenyl)cyclohexyl)1-hydroxybenzene obtained in this manner by the hydrogenation of 1,4-bis(4-hydroxyphenyl)-1-cyclohexene may be purified, if necessary. In order to purify the 4-(4'-(4"-hydroxyphenyl)cyclohexyl)-1-hydroxybenzene obtained, the reaction mixture obtained is first filtered to remove the catalyst used therefrom, and then the filtrate is subjected to crystallization and filtration, and the obtained solid product is dried in the conventional manners.

The 4-(4'-(4"-hydroxyphenyl)cyclohexyl)-1-hydroxybenzene of the invention is such a cyclohexane derivative that it has two substituents attached to different carbon atoms on the cyclohexane ring, and hence it has stereoisomers. that is, cis- and trans-isomer. Accordingly, the hydrogenation of the 1,4-bis(4-hydroxyphenyl)-1-cyclohexene provides a mixture of cis-isomer and trans-isomer of 4-(4'-(4"-hydroxyphenyl)cyclohexyl)-1-hydroxybenzene. The ratio of the cis-isomer to the trans-isomer of 4-(4'-(4"-hydroxyphenyl)cyclohexyl)-1-hydroxybenzene is usually in the range of 50/50 to 70/30, although depending upon the reaction conditions employed.

According to the invention, 4-(4'-(4"-hydroxyphenyl)-cyclohexyl)-1-hydroxybenzene obtained by the hydrogenation of 1,4-bis(4-hydroxyphenyl)-1-cyclohexene as mentioned above may be separated to the cis- and trans-isomer by various methods known per se, such as recrystallization from suitable solvents or column chromatography, and if necessary, the cis- and trans-isomer may be purified, respectively. Alternatively, the obtained 4-(4'-(4"-hydroxyphenyl)cyclohexyl)-1-hydroxybenzene may be subjected to isomerization reactions which are known with cyclohexane compounds such as an optical isomerization method or an isomerization catalyst method to provide selectively one of the isomers.

More particularly, 1,4-bis(4-hydroxyphenyl)-1-cyclohexene is hydrogenated, and the resulting reaction mixture which contains 4-(4'-(4"-hydroxyphenyl)cyclohexyl)-1-hydroxybenzene is subjected to conventional purification methods to provide a purified product, and the product is then dissolved in an organic solvent which is suitably used in column separation processes, such as methanol, acetonitrile or tetrahydrofuran, or alternatively, the reaction mixture obtained is subjected to solvent replacement by an organic solvent which is suitably used in column separation processes, such as methanol, acetonitrile or tetrahydrofuran. Then, the resulting solution of the product or the solution of the reaction mixture in such an organic solvent as mentioned above is subjected to cis-trans separation operations by a suitable means such as preparative high performance liquid chromatography making use of difference of retention time so that the cis- and trans-isomer, that is, 4-(trans-4'-(4"-hydroxyphenyl)cyclohexyl)-1-hydroxybenzene and 4-(cis-4'-(4"-hydroxyphenyl) cyclohexyl) 1-hydroxybenzene, are separately obtained.

As described above, according to the invention, either trans-isomer, i.e., 4-(trans-4'-(4"-hydroxyphenyl) cyclohexyl)-1-hydroxybenzene or cis-isomer, i.e., 4-(cis-4'-(4"-hydroxyphenyl)-cyclohexyl)-1-hydroxybenzene is separately obtained. Among these streoisomers, the trans-isomer is expected to be useful as a raw material or a component of liquid crystal compound.

The third one of the diphenols of the invention expressed by the general formula (I) is 4,4"-dihydroxy-p-terphenyl which is represented by the general formula (Ic)

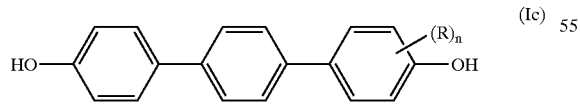

(Ic)

wherein R is an alkyl group of 1–4 carbon atoms, and n is an integer of 1–3.

Accordingly, there are mentioned as preferred examples of the 4,4"-dihydroxy-p-terphenyls of the invention:

4,4"-dihydroxy-3"-methyl-p-terphenyl,
4,4"-dihydroxy-2"-methyl-p-terphenyl,
4,4"-dihydroxy-3"-ethyl-p-terphenyl,
4,4"-dihydroxy-2"-ethyl-p-terphenyl,
4,4"-dihydroxy-3"-n-propyl-p-terphenyl,
4,4"-dihydroxy-2"-n-propyl-p-terphenyl,
4,4"-dihydroxy-3"-isopropyl-p-terphenyl,
4,4"-dihydroxy-2"-isopropyl-p-terphenyl,
4,4"-dihydroxy-3"-n-butyl-p-terphenyl,
4,4"-dihydroxy-2"-n-butyl-p-terphenyl,
4,4"-dihydroxy-3"-isobutyl-p-terphenyl,
4,4"-dihydroxy-2"-isobutyl-p-terphenyl,
4,4"-dihydroxy-3"-s-butyl-p-terphenyl,
4,4"-dihydroxy-2"-s-butyl-p-terphenyl,
4,4"-dihydroxy-3"-t-butyl-p-terphenyl,
4,4"-dihydroxy-2"-t-butyl-p-terphenyl,
4,4"-dihydroxy-3",6"-dimethyl-p-terphenyl,
4,4"-dihydroxy-3",5"-dimethyl-p-terphenyl,
4,4"-dihydroxy-2",3",6"-trimethyl-p-terphenyl,
4,4"-dihydroxy-2",3",5"-trimethyl-p-terphenyl,
4,4"-dihydroxy-3"-isopropyl-6"-methyl-p-terphenyl,
4,4"-dihydroxy-3"-isopropyl-5"-methyl-p-terphenyl,
4,4"-dihydroxy-3"-t-butyl-6"-methyl-p-terphenyl,
4,4"-dihydroxy-3"-t-butyl-5"-methyl-p-terphenyl,
4,4"-dihydroxy-3",5"-di-t-butyl-p-terphenyl, and
4,4"-dihydroxy-3",5"-diisopropyl-p-terphenyl.

Among these are in particular preferred:

4,4"-dihydroxy-3"-methyl-p-terphenyl,
4,4"-dihydroxy-3"-ethyl-p-terphenyl,
4,4"-dihydroxy-3"-isopropyl-p-terphenyl,
4,4"-dihydroxy-3"-t-butyl-p-terphenyl,
4,4"-dihydroxy-3",5"-dimethyl-p-terphenyl,
4,4"-dihydroxy-3"-isopropyl-5"-methyl-p-terphenyl,
4,4"-dihydroxy-3",5"-di-t-butyl-p-terphenyl, and
4,4"-dihydroxy-3",5"-diisopropyl-p-terphenyl.

The 4,4"-dihydroxy-p-terphenyl of the invention has lower alkyl groups only on one of the terminal hydroxyphenyl groups of the molecule and hence has an unsymmetrical structure. Such 4,4"-dihydroxy-p-terphenyls having an unsymmetrical structure are superior, for example, in solubility in various organic solvents to such 4,4"-dihydroxy-p-terphenyls having a symmetrical structure, so that such unsymmetrical 4,4"-dihydroxy-p-terphenyls are useful as raw materials for production of synthetic resins such as liquid crystalline polyesters, polycarbonates or polyurethanes, or as raw materials for production of photoresists for display elements or semiconductors.

The 4,4"-dihydroxy-p-terphenyl of the invention is obtained by thermally decomposing hydroxyphenyl substituted cyclohexylidene bisphenol represented by the aforementioned general formula (II)

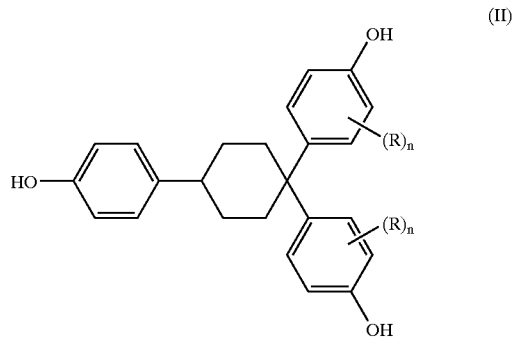

(II)

wherein R is an alkyl group of 1–4 carbon atoms and n is an integer of 1–3, preferably in the presence of an alkali catalyst, as described hereinbefore, and then by subjecting to the resulting reaction mixture to dehydrogenation.

The hydroxyphenyl substituted cyclohexylidene bisphenol represented by the general formula (II) and used as the starting material in the above-mentioned process are exemplified by those which have alkyl groups only on one of the two phenolic nuclei among those which are exemplified hereinbefore.

In this way, according to the invention, the hydroxyphenyl substituted cyclohexylidene bisphenol is thermally decomposed preferably in the presence of an alkali catalyst to generate 1,4-bis(4-hydroxyphenyl)-1-cyclohexene, as mentioned herein-above, and the resulting reaction mixture thus containing the 1,4-bis(4-hydroxyphenyl)-1-cyclohexene is subjected to dehydrogenation so that the cyclohexene ring of the 1,4-bis(4-hydroxyphenyl)-1-cyclohexene is dehydrogenated, thereby providing 4,4"-dihydroxy-p-terphenyl which has an alkyl substituent only on one of the 4-hydroxyphenyl group of the terminal of the molecule and hence an unsymmetrical structure.

The processes as above described are suitably employed as processes for the production of 4,4"-dihydroxy-p-terphenyls in general in which the reaction is carried out under industrially feasible reaction conditions using industrially readily available raw materials. Therefore, as a further aspect of the invention, the further process for the production of 4,4"-dihydroxy-p-terphenyls in general including the aforementioned alkyl substituted 4,4"-dihydroxy-p-terphenyls having the general formula (Ic) will now be described.

According to the invention, the hydroxyphenyl substituted cyclohexylidene bisphenol represented by the general formula (II')

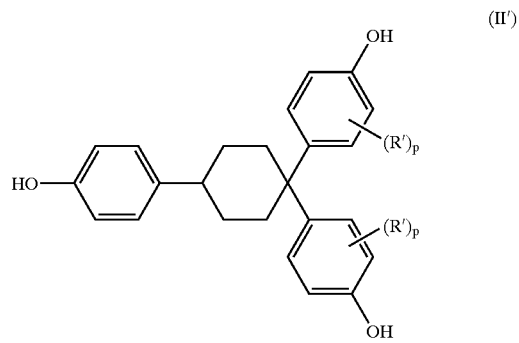

(II')

wherein R' is independently an alkyl, an alkoxyl or a haloalkoxyl group each having 1–12 carbon atoms, a cycloalkyl, a cycloalkoxyl or a halocycloalkoxyl group each having 5 or 6 carbon atoms, a phenyl group or a hydroxyl group, and p is 0 or an integer of 1–3, are thermally decomposed, as mentioned hereinbefore, and then the resulting reaction mixture is subjected to dehydrogenation, thereby providing 4,4"-dihydroxy-p-terphenyl represented by the general formula (Ic')

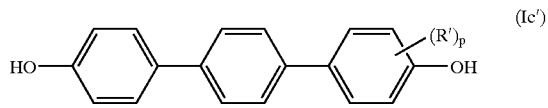

(Ic')

wherein R' and p are the same as above.

Further according to the invention, 4-(4'-hydroxyphenyl)-cyclohexanone is reacted with a substituted phenol represented by the general formula (III')

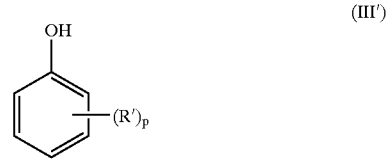

(III')

wherein R' and p are the same as above, in the presence of an acid catalyst, to provide a reaction mixture which contains the hydroxyphenyl substituted cyclohexylidene bisphenol represented by the general formula (II')

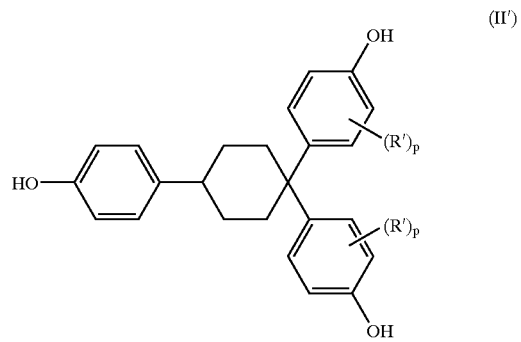

(II')

wherein R' and p are the same as above, and the resulting reaction mixture is thermally decomposed and then is subjected to dehydrogenation, as described hereinbefore, thereby providing 4,4"-dihydroxy-p-terphenyl having the above-mentioned general formula (Ic').

In the hydroxyphenyl substituted cyclohexylidene bisphenol represented by the general formula (II') used as a raw material for the process of the production of 4,4"-dihydroxy-p-terphenyls in manners as described above, R' is independently an alkyl, an alkoxyl or a haloalkoxyl group each having 1–12 carbon atoms, a cycloalkyl, a cycloalkoxyl or a halocycloalkoxyl group each having 5 or 6 carbon atoms, a phenyl or a hydroxyl group, and p is 0 or an integer of 1–3.

The alkyl group of 1–12 carbon atoms includes, for example, methyl or ethyl group, and in addition, an alkyl group of three or more carbon atoms, linear or branched, such as isopropyl, t-butyl, n-heptyl or n-decyl group. The cycloalkyl group having five or six carbon atoms includes, for example, cyclopentyl or cyclohexyl group.

The alkoxyl group of 1–12 carbon atoms includes, for example, methoxyl or ethoxyl group, and in addition, an alkoxyl group of three or more carbon atoms, linear or branched, such as isopropoxyl, t-butoxyl, s-butoxyl, n-heptoxyl or n-decyloxyl group. The cycloalkoxyl group having five or six carbon atoms includes, for example, cyclopentoxyl or cyclohexoxyl group.

The haloalkoxyl group of 1–12 carbon atoms includes, for example, monochloromethoxyl, dichloromethoxyl, monochloroethoxyl, monochloroisopropoxyl, monobromomethoxyl, dibromomethoxyl, monobromoethoxyl, difluoromethoxyl or trifluoromethoxyl group. The halocycloalkoxyl group of five or six carbon atoms includes, for example, chlorocyclopentoxyl or chlorocyclohexoxyl group.

Among these substituents, it is preferred that R' is an alkyl, an alkoxyl or a haloalkoxyl group each having 1–6 carbon atoms, a phenyl or a hydroxyl group. Accordingly, additional examples of the hydroxyphenyl substituted cyclohexylidene bisphenol represented by the general formula (II') are mentioned as follows:

1-(4-hydroxyphenyl)-4,4-bis(3-n-heptyl-4-hydroxyphenyl)-cyclohexane,
1-(4-hydroxyphenyl)-4,4-bis(3-cyclohexyl-4-hydroxyphenyl)-cyclohexane,
1-(4-hydroxyphenyl)-4,4-bis(3-cyclohexyl-6-methyl-4-hydroxyphenyl)cyclohexane,
1-(4-hydroxyphenyl)-4,4-bis(3,5-dicyclohexyl-4-hydroxyphenyl)cyclohexane,
1-(4-hydroxyphenyl)-4,4-bis(3-methoxy-4-hydroxyphenyl)-cyclohexane,
1-(4-hydroxyphenyl)-4,4-bis(2-methoxy-4-hydroxyphenyl)-cyclohexane,
1-(4-hydroxyphenyl)-4,4-bis(3-t-butoxy-4-hydroxyphenyl)-cyclohexane,
1-(4-hydroxyphenyl)-4,4-bis(2-monochloromethoxy-4-hydroxyphenyl)cyclohexane,
1-(4-hydroxyphenyl)-4,4-bis(3-trifluoromethoxy-4-hydroxyphenyl)cyclohexane,
1-(4-hydroxyphenyl)-4,4-bis(3-phenyl-4-hydroxyphenyl)-cyclohexane,
1-(4-hydroxyphenyl)-4,4-bis(3,5-diphenyl-4-hydroxyphenyl)-cyclohexane,
1-(4-hydroxyphenyl)-4,4-bis(2,4-dihydroxyphenyl)cyclohexane,
1-(4-hydroxyphenyl)-4,4-bis(3,4-dihydroxyphenyl)cyclohexane, and
1-(4-hydroxyphenyl)-4,4-bis(2,3,4-trihydroxyphenyl)cyclohexane.

In the process of the invention, the thermal decomposition of the above-mentioned hydroxyphenyl substituted cyclohexylidene bisphenol is carried out in the same manner as mentioned hereinabove. According to the invention, when an alkali catalyst is used in the thermal decomposition, an acid is added to the reaction mixture to neutralize the alkali catalyst after the completion of the thermal decomposition reaction of the hydroxyphenyl substituted cyclohexylidene bisphenol, to provide a water-containing oily reaction mixture. If necessary, after the resulting product or 1,4-bis(4-hydroxyphenyl)-1-cyclohexene is separated from the water-containing oily reaction mixture and purified, it is supplied to the next step or dehydrogenation step.

More specifically, an organic solvent such as methyl isobutyl ketone and water are added to the water-containing oily reaction mixture and the salt generated by the neutralization of the alkali catalyst with an acid and the solvent used in the thermal decomposition reaction (for example, tetraethylene glycol) are separated from the reaction mixture into the water layer, and the oil layer is separated from the water layer. Then, the solvent used (for example, methyl isobutyl ketone) is removed from the oil layer by distillation, for example, and then a crystallization solvent is added to the resulting distillation residue to effect crystallization to provide purified 1,4-bis(4-hydroxyphenyl)-1-cyclohexene as the reaction product of the thermal decomposition reaction of the hydroxyphenyl substituted cyclohexylidene bisphenol.

However, when an alkali catalyst is used in the thermal decomposition of the hydroxyphenyl substituted cyclohexylidene bisphenol, it is preferred from the standpoint of simplicity of reaction steps that an acid is added to the reaction mixture to neutralize the alkali catalyst after the completion of the thermal decomposition reaction of the hydroxyphenyl substituted cyclohexylidene bisphenol, and the thus treated reaction mixture is used as it is without purification operation such as crystallization or filtration as the starting material in the next step or in the reaction of dehydrogenation. In the same manner, when an alkali catalyst is not used in the thermal decomposition of the hydroxyphenyl substituted cyclohexylidene bisphenol, it is also preferred from the same reason as above that the reaction mixture is used as it is without purification operation such as crystallization or filtration as the starting material in the next step or in the reaction of dehydrogenation.

As mentioned above, the hydroxyphenyl substituted cyclohexylidene bisphenol is thermally decomposed and then the resulting reaction mixture is subjected to dehydrogenation thereby providing the desired 4,4"-dihydroxy-p-terphenyl. In this manner, starting with the hydroxyphenyl substituted cyclohexylidene bisphenol, the desired 4,4"-dihydroxy-p-terphenyl is obtained in yields usually of about 75% or more.

The dehydrogenation process of the reaction mixture obtained by the thermal decomposition of the hydroxyphenyl substituted cyclohexylidene bisphenol is now described in detail. According to the process of the invention, the reaction mixture obtained by the thermal decomposition of the hydroxyphenyl substituted cyclohexylidene bisphenol is subjected to dehydrogenation usually in the presence of a dehydrogenation catalyst.

As the dehydrogenation catalyst, any known one may be used. Therefore, it is exemplified by, for example, nickel catalysts such as Raney nickel, reduced nickel or nickel supporting catalysts, cobalt catalysts such as Raney cobalt, reduced cobalt or cobalt supporting catalysts, copper catalysts such as Raney copper, palladium catalysts such as palladium oxide, palladium black or palladium/carbon catalyst, platinum catalysts such as platinum black or platinum/carbon catalyst, rhodium catalysts, chromium catalysts or copper-chromium catalysts. Among these exemplified, platinum group catalysts such as palladium group catalysts are preferred and, in particular, palladium catalysts are most preferred. The dehydrogenation catalyst is used usually in an amount of 0.1–20 parts by weight, preferably in an amount of 0.2–10 parts by weight, in relation to 100 parts by weight of the starting material, the hydroxyphenyl substituted cyclohexylidene bisphenol.

The dehydrogenation process may be carried out in the presence or absence of a hydrogen acceptor, but it is preferred that the dehydrogenation process is carried out in the presence of a hydrogen acceptor. The hydrogen acceptor usable includes, for example, styrenes such as α-methylstyrene, nitrobenzene, methyl isobutyl ketone or phenols, although not specifically limited to these examples.

The dehydrogenation of the reaction mixture obtained by the thermal decomposition of hydroxyphenyl substituted cyclohexylidene bisphenol is carried out usually at a temperature of 100–250° C., preferably at a temperature of 130–200° C. The dehydrogenation of the reaction mixture obtained by the thermal decomposition of hydroxyphenyl substituted cyclohexylidene bisphenol may be carried out in gas phase, however, it is preferred from the standpoint of easier operation that it is carried out in liquid phase in which a reaction solvent is used. It is also preferred that as the reaction solvent, the same solvent as that used in the thermal decomposition of the hydroxyphenyl substituted cyclohexylidene bisphenol is used as it is from the standpoint of simplification of process. The dehydrogenation is carried out preferably at normal pressures.

Under the reaction conditions as mentioned above, the dehydrogenation of the reaction mixture obtained by the thermal decomposition of the hydroxyphenyl substituted cyclohexylidene bisphenol is completed usually in three to six hours, providing the 4,4"-dihydroxy-p-terphenyl of the invention in yields of about 75% or more in relation to the starting material, the hydroxyphenyl substituted cyclohexylidene bisphenol.

After the dehydrogenation of the reaction mixture obtained by the thermal decomposition of the hydroxyphenyl substituted cyclohexylidene bisphenol, the catalyst used is separated from the resulting reaction mixture by conventional methods and then the filtrate is subjected to crystallization and filtration to provide a crude product of 4,4"-dihydroxy-p-terphenyl of the invention. If necessary, the crude product is further crystallized and filtered to provide a highly purified product.

According to the invention, as set out above, 4,4"-dihydroxy-p-terphenyls having the general formula (Ic') are obtained in this manner, which are exemplified, for example, 4,4"-dihydroxy-p-terphenyl,
4-hydroxy-3"-trifluoromethoxy-4"-hydroxy-p-terphenyl,
4-hydroxy-3"-cyclohexyl-6"-methyl-4"-hydroxy-p-terphenyl,
4-hydroxy-3"-n-heptyl-4"-hydroxy-p-terphenyl,
4-hydroxy-3"-cyclohexyl-4"-hydroxy-p-terphenyl,
4-hydroxy-3",5"-dicyclohexyl-4"-hydroxy-p-terphenyl,
4-hydroxy-3"-methoxy-4"-hydroxy-p-terphenyl,
4-hydroxy-2"-methoxy-4"-hydroxy-p-terphenyl,
4-hydroxy-3"-t-butoxy-4"-hydroxy-p-terphenyl,
4-hydroxy-2"-monochloromethoxy-4"-hydroxy-p-terphenyl,
4-hydroxy-3"-phenyl-4"-hydroxy-p-terphenyl,
4-hydroxy-3",5"-diphenyl-4"-hydroxy-p-terphenyl,
4-hydroxy-2",4"-dihydroxy-p-terphenyl,
4-hydroxy-3",4"-dihydroxy-p-terphenyl, and
4-hydroxy-2",3",4"-trihydroxy-p-terphenyl, Further according to the invention, the reaction is effected between 4-(4'-hydroxyphenyl)cyclohexanone and the substituted phenol having the general formula (III') in the presence of an acid catalyst to generate the hydroxyphenyl substituted cyclohexylidene bisphenol expressed by the general formula (II'), the hydroxyphenyl substituted cyclohexylidene bisphenol is thermally decomposed, and then the resulting reaction mixture is subjected to dehydrogenation as described hereinabove, thereby also providing 4,4"-dihydroxy-p-terphenyl having the general formula (Ic').

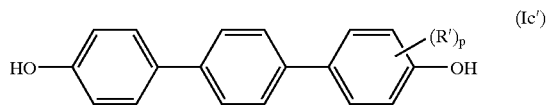

(Ic')

Also in this process, as mentioned above, the intermediate product, that is, the hydroxyphenyl substituted cyclohexylidene bisphenol or its thermal decomposition reaction product may be isolated after the completion of the reaction and, if necessary, after they are purified, they may be used as the starting materials in the next step. Alternatively, after the intermediate product or its thermal decomposition reaction product is neutralized or the catalyst used is removed therefrom if necessary, or the resulting water layer is removed or the organic solvent, the starting materials used or the volatile by-products formed are removed therefrom by distillation under reduced pressure if necessary, they may be used as the starting materials in the next step (without purification by crystallization and filtration, for example).

However, according to the invention, the latter is preferred since it needs no steps of isolation or purification of intermediate products. That is, it is preferred that the resulting reaction mixture is neutralized or the catalyst used is removed therefrom, without isolation and purification thereof, after the completion of the reaction, and is used as the starting materials in the next step.

In order to obtain the hydroxyphenyl substituted cyclohexylidene bisphenol having the general formula (II') by the reaction of 4-(4-hydroxyphenyl)cyclohexanone and the substituted phenol having the general formula (III') in the presence of an acid catalyst, a process described in Japanese Patent Laid-Open No. 2000-63308 may be employed, for example.

There may be mentioned as examples of the substituted phenol, for example, phenol, o- or m-cresol, 2,3-, 2,5-, 2,6-, 3,5- or 3,6-xylenol, 2,3,5- or 2,3,6-trimethylphenol, 2-ethylphenol, 3-ethylphenol, 2-n-proylphenol, 3-n-proylphenol, 2-isoproylphenol, 3-isoproylphenol, 2-n-butylphenol, 3-n-butylphenol, 2-isobutylphenol, 3-isobutylphenol, 2-s-butylphenol, 3-s-butylphenol, 2-isoproyl-5-methylphenol, 2-t-butyl-5-methylphenol, 2,6-di-t-butylphenol, 2-n-heptylphenol, 2-cyclohexylphenol, 2,6-dicyclo-hexylphenol, 3-methyl-6-cyclohexylphenol, 2-methoxyphenol, 3-methoxyphenol, 2-t-butoxyphenol, 3-chloromethoxyphenol, 2-trifluoromethoxyphenol, o-phenylphenol, 2,6-diphenylphenol, resorcinol, catechol or pyrogallol.

In the reaction of the substituted phenol and 4-(4'-hydroxyphenyl)cyclohexanone, the substituted phenol is used in an amount of 4–20 mol parts in relation to 100 mol parts of 4-(4'-hydroxyphenyl)cyclohexanone. Further in the reaction of the substituted phenol and 4-(4-hydroxyphenyl)cyclohexanone, reaction solvents may or may not be used. The reaction solvent usable includes, for example, aliphatic alcohols, aromatic hydrocarbons or a mixture of these. The aliphatic alcohol usable includes, for example, methanol, ethanol, isopropyl alcohol, n-propyl alcohol, t- butyl alcohol, isobutyl alcohol or n-butyl alcohol in consideration of solubility of the reaction product as well as the starting materials, the reaction conditions employed and the economical efficiency of the reaction. The aromatic hydrocarbon usable includes, for example, toluene, xylene or cumene. When a solvent is used, it is used in the range of 100–500 parts by weight of 4-(4-hydroxyphenyl)cyclohexanone, although the amount is not limited to the amount mentioned above.

In turn, dried hydrogen chloride gas is used as the acid catalyst, but the acid catalyst usable is not limited to the above, and for example, hydrochloric acid, sulfuric acid, anhydrous sulfuric acid, p-toluenesulfonic acid, methanesulfonic acid, trifluoromethanesulfonic acid, oxalic acid, formic acid, phosphoric acid, trichloroacetic acid or trifluoroacetic acid may be also used. The catalyst, for example, dried hydrogen chloride gas, is used preferably in such an amount that the reaction system is saturated therewith. In addition, a cocatalyst such as mercaptan (for example, octylmercaptan) may be used in order to promote the reaction.

The reaction is carried out usually at a temperature of 20–80° C., preferably at a temperature of 20–50° C., with stirring over a period of 2–48 hours, preferably 6–24 hours, while blowing dried hydrogen chloride gas into the reaction mixture.

After the completion of the reaction, an alkali is added to the resulting reaction mixture to neutralize the acid catalyst used, and then a crystallization solvent is added to the resulting water layer or, the resulting water layer is removed from the reaction mixture, and if necessary after distillation of the resulting oil layer, a crystallization solvent is added to the resulting distillation residual, thereby to crystallize crude crystals, followed by recrystallization from an appropriate solvent to provide purified product of the hydroxyphenyl substituted cyclohexylidene bisphenol. According to the invention, either the crude crystals or purified products may be used as the starting material for the thermal decomposition reaction of the next step.

However, it is preferred according to the invention that after the completion of the reaction, an alkali is added to the resulting reaction mixture to neutralize the acid catalyst used, the resulting water layer is removed from the reaction mixture, and the resulting oily reaction mixture is used as the starting material for the thermal decomposition of the next step from the standpoint of simplicity of reaction steps, as mentioned hereinbefore.

The oily reaction mixture containing the hydroxyphenyl substituted cyclohexylidene bisphenol is thermally decomposed preferably in the presence of an alkali catalyst, and the resulting reaction mixture is subjected to dehydrogenation, as described hereinabove, thereby providing 4,4"-dihydroxy-p-terphenyl having the general formula (Ic').

As described above, according to the process of the invention, since all the reactions inclusive of the case where the process is started by using substituted phenols and 4-(4'-hydroxyphenyl)-cyclohexanone can be carried out under normal pressure or under reduced pressure, the process of the invention needs no special reaction apparatus, for example, for high pressure reactions. Thus, according to the process of the invention, the desired 4,4"-dihydroxy-p-terphenyl is obtained in high yields and in high purity by using raw materials which are easily available and by carrying out reactions under industrially feasible reaction conditions.

Industrial Availability

The 4,4"-dihydroxy-p-terphenyls of the invention have such an unsymmetrical structure in which only the terminal hydroxyphenyl group of the molecule has lower alkyl group substituents so that they are superior in, for example, solubility in various organic solvents to such 4,4"-dihydroxy-p-terphenyls that have a symmetrical structure. Accordingly, the 4,4"-dihydroxy-p-terphenyls of the invention are useful as raw materials for production of various kinds of synthetic resins such as liquid crystalline polyesters, polycarbonates, polyurethanes, but also as raw materials for photoresists for use in the production of display elements or semiconductors, or as raw materials for organic electroluminescence elements.

The 1,4-bis(4-hydroxyphenyl)-1-cyclohexenes of the invention are themselves useful not only as intermediate raw materials for production of various kinds of resins similarly to the 4,4"-dihydroxy-p-terphenyls as mentioned above, but also useful as intermediate raw materials for the production of a variety of such resins as mentioned above.

The 4-(4'-(4"-hydroxyphenyl)cyclohexyl)-1-hydroxybenzenes of the invention are also themselves useful as intermediate raw materials for production of various kinds of resins or liquid crystal materials similarly to the 4,4"-dihydroxy-p-terphenyls as mentioned above, but also useful as intermediate raw materials for production of the 4,4"-dihydroxy-p-terphenyls as above mentioned.

In addition, according to the process of the invention, the desired 4,4"-dihydroxy-p-terphenyls are obtained in high yields and in high purity by using raw materials which are easily available and by carrying out reactions under industrially feasible reaction conditions without use of any special reaction apparatus.

EXAMPLES

The invention is explained with reference to examples, however, the invention is not limited to these examples.

Example A

Production of 1,4-bis(4-hydroxyphenyl)-1-cyclohexenes

Example 1

Production of 1,4-bis(4-hydroxyphenyl)-1-cyclohexene 30.1 g (0.0836 mol) of 1-(4-hydroxyphenyl)-4,4-bis(4-hydroxyphenyl)cyclohexane, 0.8 g of 48% aqueous solution of sodium hydroxide and 15.1 g of tetraethylene glycol were placed in a reaction vessel (200 mL capacity four necked flask). The atmosphere inside the reaction vessel was displaced with nitrogen gas and then the flask was evacuated so that it was put under vacuum of 100 mmHg. The thermal decomposition reaction was carried out at a temperature of about 210° C. over a period of about three hours under the reduced pressure. The reaction was ceased when no more distillate was obtained. After the completion of reaction, 50% aqueous solution of acetic acid was added to the resulting reaction mixture to neutralize the reaction mixture and put it at a pH of about 6, thereby providing 49.2 g of a water-containing oily substance.

Water was added to the thus obtained water-containing oily substance to move the salt formed by the neutralization with the acetic acid and tetraethylene glycol used as the solvent to the water layer and the water layer was removed from the water-containing oily substance. Then methanol was added to the resulting oil layer so that the desired product was crystallized. The obtained solid was collected by filtration and dried to provide 12.0 g of 1,4-bis(4-hydroxyphenyl)-1-cyclohexene as white crystals having a purity of 93.5% (high performance liquid chromatography). The reaction yield was found to be 57.1 mol % based on the starting material, that is, 1-(4-hydroxyphenyl)-4,4-bis(4-hydroxyphenyl)-cyclohexane.

Melting point (differential thermal analysis (DTA) method): 251° C. Molecular weight (mass spectrometry, (M+2H)$^+$): 268 Proton NMR (400 MHz, solvent DMSO-d, δ (ppm)): 1.69–1.80 (1H, m), 1.89–1.95 (1H, m), 2.13–2.23 (1H, m), 2.33–2.50 (3H, m), 2.63–2.73 (1H, m), 6.05 (1H, d, J=3.2 Hz), 6.70 (4H, t, J=8.0 Hz), 7.07 (2H, d, J=8.0 Hz), 7.24 (2H, d, J=8.4 Hz), 9.15 (1H, s), 9.35 (1H, s).

Reference Example 1

Production of 4,4"-dihydroxy-p-terphenyl 5.3 g of 1,4-bis(4-hydroxyphenyl)-1-cyclohexene obtained in Example 1, 6.0 g of α-methylstyrene and 0.5 g of palladium/carbon catalyst (containing 50% by weight of water) were placed in a reaction vessel (200 mL capacity four necked flask). The atmosphere inside the reaction vessel was displaced with nitrogen gas, the mixture in the flask was heated to 163° C. under normal pressure and the reaction was carried out with stirring for three hours.

After the completion of the reaction, 136 g of dimethylformamide was added to the resulting reaction mixture and mixed. The palladium/carbon catalyst was removed from the reaction mixture by filtration, and then the solvent used was removed by distillation, to provide distillation residue which contained the desired product. Methanol was added to the distillation residue to carry out crystallization, followed by filtration. The thus obtained solid was dried to provide 4.5 g of 4,4"-dihydroxy-p-terphenyl as white crystals having a purity of 99.0% (as measured by high performance liquid chromatography). The reaction yield was 89.1% based on the 1,4-bis(4-hydroxyphenyl)-1-cyclohexene used.

Example 2

Production of 1-(3-methyl-4-hydroxyphenyl)-4-(4-hydroxyphenyl)-1-cyclohexene 60.9 g (0.157 mol) of 1-(4-hydroxyphenyl)-4,4-bis(3-methyl-4-hydroxyphenyl)cyclohexane, 0.6 g of 48% aqueous solution of sodium hydroxide and 18.0 g of tetraethylene glycol were placed in a reaction vessel (300 mL capacity four necked flask). The atmosphere inside the reaction vessel was displaced with nitrogen gas and the flask was then evacuated to put it under vacuum of 40 mmHg. The thermal decomposition reaction was carried out at a temperature of about 210° C. over a period of about three hours under the reduced pressure. The reaction was ceased when no more distillate was obtained. After the completion of reaction, 50% aqueous solution of acetic acid was added to the resulting reaction mixture to neutralize the reaction mixture and put it at a pH of about 6, thereby providing 63.4 g of a water-containing oily substance.

Methyl isobutyl ketone and water were added to the thus obtained water-containing oily substance to move the salt formed by the neutralization with acetic acid and tetraethylene glycol used as the solvent to the water layer and the water layer was removed from the water-containing oily substance. Thereafter the methyl isobutyl ketone was removed by distillation and toluene was added to the residual oil layer to effect crystallization. The thus obtained solid was dried to provide 26.5 g of 1-(3-methyl-4-hydroxyphenyl)-4-(4-hydroxyphenyl)-1-cyclohexene as white crystals having a purity of 97.7% (high performance liquid chromatography). The reaction yield was found to be 80.8 mol % based on the 1-(4-hydroxyphenyl)-4,4-bis(3-methyl-4-hydroxyphenyl)cyclohexane used.

Melting point (DTA method): 201° C. Molecular weight (mass spectrometry, $M^+$): 280 Proton NMR (400 MHz, solvent DMSO-d, δ (ppm)): 1.71–1.79 (1H, m), 1.88–1.97 (1H, m), 2.11 (3H, s), 2.16–2.24 (1H, m), 2.28–2.50 (4H, m), 2.63–2.72 (1H, m), 6.02 (1H, d, J=3.2 Hz), 6.70 (3H, t, J=9.6 Hz), 7.06 (4H, d, J=8.0 Hz), 9.14 (1H, s), 9.22 (1H, s).

Example 3

Production of 1-(3-isopropyl-4-hydroxyphenyl)-4-(4-hydroxyphenyl)-1-cyclohexene 459 g (1.03 mol) of 1-(4-hydroxyphenyl)-4,4'-bis(3-isopropyl-4-hydroxyphenyl)cyclohexane, 9.2 g of 48% aqueous solution of sodium hydroxide and 200 g of tetraethylene glycol were placed in a reaction vessel (1L capacity four necked flask), and then 385 g of water-containing oily substance were obtained in the same manner as in Example 2.

The water-containing oily substance was treated in the same manner as in Example 2, 112 g of 1-(3-isopropyl-4-hydroxyphenyl)-4-(4-hydroxyphenyl)-1-cyclohexene was obtained as white crystals having a purity of 99.4% (high performance liquid chromatography). The yield was 85.1 mol % based on the 1-(4-hydroxyphenyl)-4,4'-bis(3-isopropyl-4-hydroxyphenyl)cyclohexane used.

Melting point (DTA method): 178° C. Molecular weight (mass spectrometry, $(M+H)^+$): 309 Proton NMR (400 MHz, solvent DMSO-d, δ (ppm)): 1.17 (6H, d, J=7.2 Hz), 1.68–1.81 (1H, m), 1.89–1.97 (1H,m), 2.13–2.23 (1H, m), 2.31–2.41 (1H, m), 2.42–2.48 (2H, d, J=4.0 Hz), 2.63–2.72 (1H, m), 3.20 (1H, q, J=6.8 Hz), 6.03 (1H, d, J=2.0 Hz), 6.70 (2H, d, J=8.8 Hz), 6.72 (1H, d, J=8.0 Hz), 7.02–7.08 (3H, m), 7.18 (1H, d, J=2.4 Hz), 9.14 (1H, s), 9.22 (1H, s).

Example 4

Production of 1-(3-t-butyl-4-hydroxyphenyl)-4-(4-hydroxyphenyl)-1-cyclohexene 581 g (1.23 mol) of 1-(4-hydroxyphenyl)-4,4'-bis(3-t-butyl-4-hydroxyphenyl)cyclohexane, 11.7 g of 48% aqueous solution of sodium hydroxide and 200 g of tetraethylene glycol were placed in a reaction vessel (2L capacity four necked flask), and the thermal decomposition reaction was carried out at a temperature of 205° C. over a period of five hours, and otherwise in the same manner as in Example 2, 556 g of a water-containing oily substance was obtained.

The water-containing oily substance was treated in the same manner as in Example 2 to provide 332 g of 1-(3-t-butyl-4-hydroxyphenyl)-4-(4-hydroxyphenyl)-1-cyclohexene as white crystals having a purity of 98.8% (high performance liquid chromatography). The yield was 82.8 mol % based on the 1-(4-hydroxyphenyl)-4,4'-bis(3-t-butyl-4-hydroxyphenyl)cyclohexane used.

Melting point (DTA method): 188° C. Molecular weight (mass spectrometry, $(M+H)^+$): 323 Proton NMR (400 MHz, solvent DMSO-d, δ (ppm)): 1.36 (9H, s), 1.70–1.82 (1H, m), 1.89–1.97 (1H, m), 2.13–2.24 (1H, m), 2.31–2.41 (1H, m), 2.46 (2H, brs), 2.63–2.73 (1H, m), 6.02 (1H, brs), 6.70 (2H, d, J=8.4 Hz), 6.73 (1H, d, J=8.4 Hz), 7.06 (3H, d, J=8.4 Hz), 7.21 (1H, d, J=2.8 Hz), 9.14 (1H, s), 9.29 (1H, s)

Example 5

Production of 1-(3,5-dimethyl-4-hydroxyphenyl)-4-(4-hydroxyphenyl)-1-cyclohexene 541 g (1.80 mol) of 1-(4-hydroxyphenyl)-4,4'-bis(3,5-dimethyl-4-hydroxyphenyl)cyclohexane, 10.8 g of 48% aqueous solution of sodium hydroxide and 200 g of tetraethylene glycol were placed in a reaction vessel (2L capacity four necked flask), and the thermal decomposition reaction was carried out over a period of two hours, and otherwise in the same manner ass in Example 2, 676 g of a water-containing oily substance was obtained.

The water-containing oily substance was treated in the same manner as in Example 2 to provide 428 g of 1-(3,5-dimethyl-4-hydroxyphenyl)-4-(4-hydroxyphenyl)-1-cyclohexene as white crystals having a purity of 96.6% (high performance liquid chromatography). The yield was 78.1 mol % based on the 1-(4-hydroxyphenyl)-4,4'-bis(3,5-dimethyl-4-hydroxyphenyl)-cyclohexane used.

Melting point (DTA method): 224° C. Molecular weight (mass spectrometry, $(M+H)^+$): 295 Proton NMR (400 MHz, solvent DMSO-d, δ (ppm)): 1.67–1.79 (1H, m), 1.88–1.96 (1H, m), 2.15 (6H, s), 2.17–2.23 (1H, m), 2.29–2.39 (1H, m), 2.40–2.46 (2H, m), 2.62–2.71 (1H, m), 6.02 (1H, d, J=2.2 Hz), 6.69 (2H, d, J=8.8 Hz), 6.98 (2H, s), 7.06 (2H, d, J=8.4 Hz), 8.14 (1H, s), 9.13 (1H, s).

Example B

Production of 4-(4'-(4"-hydroxyphenyl)cyclohexyl)-1-hydroxybenzenes

Example 1

Production of 4-(4'-(4"-hydroxyphenyl)cyclohexyl)-2-methyl-1-hydroxybenzene 21 g (0.075 mol) of 1-(3-methyl-4-hydroxyphenyl)-4-(4-hydroxyphenyl)-1-cyclohexene obtained in Example 2 of Example A, 170 g of isopropyl alcohol and 2.5 g of 5% palladium/carbon catalyst (containing 50% by weight of water, available from N. E. Chemcat K.K.) were placed in a reaction vessel (1L capacity autoclave). The atmosphere inside of the reaction vessel was displaced with nitrogen gas, and then with hydrogen gas. Then, the reaction vessel was heated so that the hydrogen pressure inside the reaction vessel was adjusted at 0.2 MPa when the inside the reaction vessel reached a temperature of about 45° C.

The hydrogen absorption ceased after 30 minutes from the start of the reaction, and 60 g of dimethylformamide was added to the resulting reaction mixture and then the catalyst used was removed by filtration. The isopropyl alcohol and dimethyl-formamide were removed by distillation from the resulting filtrate to provide 21.5 g of the desired product, 4-(4'-(4"-hydroxyphenyl)cyclohexyl)-2-methyl-1-hydroxybenzene as white solid having a purity of 94.6% (high performance liquid chromatography). The yield was 96.1 mol % based on the 1-(3-methyl-4-hydroxyphenyl)-4-(4-hydroxyphenyl)-1-cyclohexene used.

Melting point (DTA method): 159° C. Molecular weight (mass spectrometry, (M–H)$^-$): 281 Proton NMR (400 MHz, solvent DMSO-d, δ (ppm)): 1.50 (2H, t, J=9.6 Hz), 1.70 (2H, brs), 1.83 (4H, d, J=7.2 Hz), 2.09 (1.8H, s), 2.11 (1.2H, s), 2.37–2.48 (0.8H, m), 2.65–2.76 (1.2H, m), 6.79 (3H, d, J=8.0 Hz), 6.85 (1H, d, J=8.0 Hz), 6.91 (1H, brs), 7.02–7.07 (2H, m), 9.00 (1H, s), 9.14 (1H, s).

Example 2

1 g of 4-(4'-(4"-hydroxyphenyl)cyclohexyl)-2-methyl-1-hydroxybenzene obtained in Example 1 was dissolved in 10 g of methanol at room temperature. The solution was injected into a preparative high performance liquid chromatography to carry out separation of cis- and trans-isomers (solvent: 60% aqueous solution of methanol; time: 40 minutes). As a result, about 50 mg of 4-(trans-4'-(4"-hydroxyphenyl)cyclohexyl)-2-methyl-1-hydroxybenzene was obtained as white crystals with a retention time of 17.6 minutes. It was found to have a purity of 99% and a melting point of 214° C. (DTA method). Furthermore, about 100 mg of 4-(cis-4'-(4"-hydroxyphenyl)cyclohexyl)-2-methyl-1-hydroxybenzene was obtained as pale yellow oily substance with a retention time of 28.2 minutes. It was found to have a purity of 99%.

The above results also show that the selectivity of trans/cis-isomers of 4-(4'-(4"-hydroxyphenyl)cyclohexyl)-2-methyl-1-hydroxybenzene obtained in Example 1 was found to be 37/63 (preparative high performance liquid chromatography).

The identification data of the trans- and cis-isomer are shown below.
Trans isomer (4-(trans-4'-(4"-hydroxyphenyl)cyclohexyl)-2-methyl-1-hydroxybenzene):

Melting point (DTA method): 214° C. Proton NMR (400 MHz, solvent DMSO-d, δ (ppm)): 1.49 (4H, t, J=9.6 Hz), 1.82 (4H, d, J=8.4 Hz), 2.09 (3H, s), 2.41 (2H, d, J=10 Hz), 6.08 (3H, d, J=7.6 Hz), 6.84 (1H, d, J=8.0 Hz), 6.91 (1H, s), 7.02 (2H, d, J=8.4 Hz), 9.06 (2H, brs).
Cis isomer (4-(cis-4'-(4"-hydroxyphenyl)cyclohexyl)-2-methyl-1-hydroxybenzene)

Proton NMR (400 MHz, solvent DMSO-d, δ (ppm)): 1.69 (4H, d, J=4.8 Hz), 1.84 (4H, s), 2.11 (3H, s), 2.71 (2H, d, J=11 Hz), 6.68–6.72 (3H, m), 6.86 (1H, d, H=8.0 Hz), 6.92 (1H, s), 7.04 (2H, d, J=7.6 Hz), 9.09 (2H, brs).

Example 3

Production of 4-(4'-(4"-hydroxyphenyl)cyclohexyl)-2-isopropyl-1-hydroxybenzene

After 12.5 g (0.040 mol) of 1-(3-isopropyl-4-hydroxyphenyl)-4-(4-hydroxyphenyl)-1-cyclohexene obtained in Example 3 of Example A, 300 g of isopropyl alcohol and 3.8 g of Raney nickel catalyst were placed in a reaction vessel (1L capacity autoclave), the atmosphere inside the reaction vessel was displaced with nitrogen gas, then with hydrogen gas, and then the autoclave was heated to adjust the hydrogen pressure in the autoclave to 0.3 MPa when the contents in the autoclave reached a temperature of about 45° C.

The hydrogen absorption ceased after about two hours from the start of the reaction. While maintaining the resulting reaction mixture at a temperature of 50° C., it was filtered to remove the catalyst used, and then the isopropyl alcohol used was removed from the resulting filtrate to provide 12.0 g of 4-(4'-(4"-hydroxyphenyl)cyclohexyl)-2-isopropyl-1-hydroxybenzene as white solid having a purity of 97.6% (high performance liquid chromatography). The yield was 94.4 mol % based on the 1-(3-isopropylyl-4-hydroxyphenyl)-4-(4-hydroxyphenyl)-1-cyclohexene used. The selectivity of trans-/cis-isomer of 4-(4'-(4"-hydroxyphenyl)cyclohexyl)-2-isopropyl-1-hydroxybenzene was found to be 64/36 (high performance liquid chromatography).

0.2 g of 4-(4'-(4"-hydroxyphenyl)cyclohexyl)-2-isopropyl-1-hydroxybenzene thus obtained was dissolved in 2 g of methanol at room temperature. The solution was injected into a preparative high performance liquid chromatography to carry out separation of cis- and trans-isomers (solvent: 78% aqueous solution of methanol; time: 200 minutes). As a result, about 100 mg of 4-(trans-4'-(4"-hydroxyphenyl)cyclohexyl)-2-isopropyl-1-hydroxybenzene was obtained as white crystals with a retention time of 8.1 minutes. It was found to have a purity of 99% (high performance liquid chromatography).

Furthermore, about 50 mg of 4-(cis-4'-(4"-hydroxyphenyl)-cyclohexyl)-2-isopropyl-1-hydroxybenzene was obtained as colorless transparent oily substance with a retention time of 13.1 minutes. It was found to have a purity of 99% (high performance liquid chromatography).

The identification data of the trans- and cis-isomers are shown below.
Trans isomer (4-(trans-4'-(4"-hydroxyphenyl)cyclohexyl)-2-iso-propyl-1-hydroxybenzene):

Melting point (DTA method): 165° C. Molecular weight (mass spectrometry, (M–H)$^-$): 309 Proton NMR (400 MHz, solvent DMSO-d, δ (ppm)): 1.16 (6H, d, J=6.8 Hz), 1.51 (4H, t, J=10.8 Hz), 1.84 (4H, d, J=7.2 Hz), 2.38–2.49 (2H, m), 3.19 (1H, q, J=6.8 Hz), 6.69 (3H, dd, J=8.0, 2.0 Hz), 6.84 (1H, dd, J=8.4, 2.4 Hz), 6.97 (1H, d, J=2.4 Hz), 7.03 (2H, d, J=8.4 Hz), 8.98 (1H, s), 9.10 (1H, s).
Cis isomer (4-(trans-4'-(4"-hydroxyphenyl)cyclohexyl)-2-isopropyl-1-hydroxybenzene):

Molecular weight (mass spectrometry, (M–H$^-$): 309 Proton NMR (400 MHz, solvent DMSO-d, δ (ppm)): 1.16 (3H, s), 1.18 (3H, s), 1.68–1.79 (4H, m), 1.79–1.92 (4H, m), 2.73 (2H, s), 3.16–3.25 (1H, m), 6.72 (3H, dd, J=8.4, 2.8 Hz), 6.86 (1H, dd, J=8.4, 2.8 Hz), 7.00 (1H, s), 7.05 (2H, d, J=8.4 Hz), 9.05 (2H, s).

Example 4

Production of 4-(4'-(4"-hydroxyphenyl)cyclohexyl)-2-t-butyl-1-hydroxybenzene 26.6 g (0.081 mol) of 1-(3-t-butyl-4-hydroxyphenyl)-4-(4-hydroxyphenyl)-1-cyclohexene obtained in Example 4 of Example A, 266 g of isopropyl alcohol and 5.5 g of Raney nickel catalyst were placed in a reaction vessel (1L capacity autoclave), and then in the same manner as in Example 3, 26.6 g of 4-(4'-(4"-hydroxyphenyl)-cyclohexyl)-2-t-butyl-1-hydroxybenzene was obtained as white crystals having a purity of 97.9% (high performance liquid chromatography). The yield was found to be 99.2 mol % based on the 1-(3-t-butyl-4-hydroxyphenyl)-4-(4-hydroxyphenyl)-1-cyclohexene. The selectivity of trans-/cis-isomers of 4-(4'-(4"-hydroxyphenyl)cyclohexyl)-2-t-butyl-1-hydroxybenzene was found to be 64/36 (high performance liquid chromatography).

0.2 g of 4-(4'-(4"-hydroxyphenyl)cyclohexyl)-2-t-butyl-1-hydroxybenzene thus obtained was dissolved in 2 g of methanol at room temperature. The solution was injected into a preparative high performance liquid chromatography to carry out separation of cis- and trans-isomers (solvent: 80% aqueous solution of methanol; time: 20 minutes). As a result, about 100 mg of 4-(trans-4'-(4"-hydroxyphenyl)cyclohexyl)-2-t-butyl-1-hydroxybenzene was obtained as white crystals with a retention time of 9.5 minutes. It was found to have a purity of 99% (high performance liquid chromatography).

Furthermore, about 50 mg of 4-(cis-4'-(4"-hydroxyphenyl)-cyclohexyl)-2-t-butyl-1-hydroxybenzene was obtained as colorless transparent oily substance with a retention time of 15.4 minutes. It was found to have a purity of 99% (high performance liquid chromatography).

The identification data of the trans- and cis-isomers are shown below.
Trans isomer (4-(tran-4'-(4"-hydroxyphenyl) cyclohexyl)-2-t-butyl-1-hydroxybenzene)

Melting point (DTA method): 185° C. Molecular weight (mass spectrometry, (M–H)$^-$): 323 Proton NMR (400 MHz, solvent DMSO-d, δ (ppm)): 1.35 (9H, s), 1.51 (4H, t, J=10.8 Hz), 1.84 (4H, d, J=8.0 Hz), 2.44 (2H, s), 6.70 (3H, dd, J=8.0, 7.6 Hz), 6.87 (1H, d, J=8.0 Hz), 6.99–7.04 (3H, m), 9.05 (1H, s), 9.10 (1H, s).
Cis isomer (4-(cis-4'-(4"-hydroxyphenyl)cyclohexyl)-2-t-butyl-1-hydroxybenzene)

Molecular weight (mass spectrometry, (M–H)$^-$): 323 Proton NMR (400 MHz, solvent DMSO-d, δ (ppm)): 1.34 (9H, s), 1.65–1.92 (8H, m), 2.74 (2H, s), 6.69 (3H, d, J=8.4 Hz), 6.86 (1H, d, J=8.4 Hz), 7.01–7.07 (3H, m), 9.08 (2H, s).

Example 5

Production of 4-(4'-(4"-hydroxyphenyl)cyclohexyl)-2,6-dimethyl-1-hydroxybenzene 19.6 g (0.063 mol) of 1-(3,5-dimethyl-4-hydroxyphenyl)-4-(4-hydroxyphenyl)-1-cyclohexene obtained in Example 5 of Example A, 300 g of isopropyl alcohol and 5.2 g of Raney nickel catalyst were placed in a reaction vessel (1L capacity autoclave), and then in the same manner as in Example 3, 18.6 g of 4-(4'-(4"-hydroxyphenyl)-cyclohexyl)-2,6-dimethyl-1-hydroxybenzene) was obtained as white crystals having a purity of 92.7% (high performance liquid chromatography). The yield was found to be 92.0 mol % based on the 1-(3,5-dimethyl-4-hydroxyphenyl)-4-(4-hydroxyphenyl)-1-cyclohexene used. The selectivity of trans-/cis-isomers of 4-(4'-(4"-hydroxyphenyl)cyclohexyl)-2,6-dimethyl-1-hydroxybenzene was found to be 69/31 (high performance liquid chromatography).

0.2 g of 4-(4'-(4"-hydroxyphenyl)cyclohexyl)-2,6-dimethyl-1-hydroxybenzene thus obtained was dissolved in 2 g of methanol at room temperature. The solution was injected into a preparative high performance liquid chromatography to carry out separation of cis- and trans-isomers (solvent: 70% aqueous solution of methanol; time: 20 minutes). As a result, about 120 mg of 4-(trans-4'-(4"-hydroxyphenyl)cyclohexyl)-2,6-dimethyl-1-hydroxybenzene was obtained as white crystals with a retention time of 9.9 minutes. It was found to have a purity of 99% (high performance liquid chromatography).

Furthermore, about 50 mg of 4-(cis-4'-(4"-hydroxyphenyl)-cyclohexyl)-2,6-dimethyl-1-hydroxybenzene was obtained as colorless transparent oily substance with a retention time of 16.1 minutes. It was found to have a purity of 99% (high performance liquid chromatography).

The identification data of the trans- and cis-isomer are shown below.
Trans isomer (4-(tran-4'-(4"-hydroxyphenyl)cyclohexyl)-2,6-dimethyl-1-hydroxybenzene)

Melting point (DTA method): 224° C. Molecular weight (mass spectrometry, (M–H)$^-$): 295 Proton NMR (400 MHz, solvent DMSO-d, δ (ppm)): 1.50 (4H, t, J=9.6 Hz), 1.83 (4H, d, J=9.2 Hz), 2.13 (6H, s), 2.35–2.45 (2H, m), 6.67 (2H, d, J=8.8 Hz), 6.77 (2H, s), 7.03 (2H, d, J=8.4 Hz), 7.91 (1H, s), 9.10 (1H, s).
Cis isomer (4-(cis-4'-(4"-hydroxyphenyl)cyclohexyl)-2,6-dimethyl-1-hydroxybenzene)

Molecular weight (mass spectrometry, (M–H)$^-$): 295 Proton NMR (400 MHz, solvent DMSO-d, δ (ppm)): 1.55–1.75 (4H, m), 1.75–1.89 (4H, m), 2.12 (6H, s), 2.65 (1H, s), 2.74 (1H, s), 6.68 (2H, d, J=7.6 Hz), 6.76 (2H, s), 7.04 (2H, d, J=8.4 Hz), 7.91 (1H, m), 9.11 (1H, s).

Example C

Production of 4,4"-dihydroxy-p-terphenyls

Example 1

Production of 4-hydroxy-3"-methyl-4"-hydroxy-p-terphenyl

Thermal Decomposition Step 50.2 g (0.129 mol) of 1-(4-hydroxyphenyl)-4,4-bis(3-methyl-4-hydroxyphenyl)cyclohexane, 0.3 g of 48% aqueous solution of sodium hydroxide and 26.3 g of tetraethylene glycol were placed in a reaction vessel (300 mL capacity four necked flask), and the atmosphere inside the flask was displaced with nitrogen gas. The flask was evacuated to a reduced pressure of about 50 mmHg, and the thermal decomposition reaction was carried out at a temperature of about 210° C. over a period of four hours. The reaction was ceased when no more distillate was obtained. After the completion of the reaction, 50% aqueous solution of acetic acid was added to the reaction mixture to neutralize the reaction mixture to a pH of about six, to provide 64.7 g of a water-containing oily substance.

Dehydrogenation Step 60.0 g of α-methylstyrene and 3.5 g of 5% palladium/carbon catalyst (containing 50% by weight of water) were additionally added to 64.7 g of the water-containing oily substance in the reaction vessel. The atmosphere inside the reaction vessel was displaced with nitrogen gas, and the reaction vessel was heated to a temperature of 165° C. under normal pressure, followed by three hour reaction with stirring.

After the completion of the reaction, 50 g of dimethylformamide was added and mixed, and then the palladium/carbon catalyst used was removed from the resulting reaction mixture by filtration, followed by removing the solvent by distillation, thereby providing distillation residual which contained the desired product. Methanol was added to the distillation residual to dissolve the residual therein, and water was added to the methanol solution so that the desired product was crystallized out. The resulting solid was collected and dried to provide 30.5 g of 4-hydroxy-3"-methyl-4"-hydroxy-p-terphenyl as white crystals having a purity of 99.1% (high performance liquid chromatography). The yield was 85.8 mol % based on the 1-(4-hydroxyphenyl)-4,4-bis(3-methyl-4-hydroxyphenyl)cyclohexane used.

Melting point (DTA method): 251.4° C. Molecular weight (mass spectrometry, ($M^+$)): 277 Proton NMR (400 MHz, solvent DMSO-d, δ (ppm)): 2.19 (s, 3H), 6.86 (dd, 3H, J=8.0 Hz, J=3.2 Hz), 7.32 (dd, 1H, J=10.2 Hz, J=2.4 Hz), 7.41 (d, 1H, J=2.4 Hz), 7.50 (d, 2H, J=8.8 Hz), 7.58 (s, 4H), 9.48 (brs.2H).

Example 2

Production of 4-hydroxy-3",5"-dimethyl-4"-hydroxy-p-terphenyl

Thermal Decomposition Step 83.2 g (0.200 mol) of 1-(4-hydroxyphenyl)-4,4-bis(3,5-dimethyl-4-hydroxyphenyl)cyclohexane, 0.4 g of 48% aqueous solution of sodium hydroxide and 32 g of tetraethylene glycol were placed in a reaction vessel (300 mL capacity four necked flask), and the atmosphere inside the flask was displaced with nitrogen gas. The flask was evacuated to a reduced pressure of about 40 mmHg, and the thermal decomposition reaction was carried out at a temperature of about 210° C. over a period of four hours. The reaction was ceased when no more distillate was obtained. After the completion of the reaction, 50% aqueous solution of acetic acid was added to the reaction mixture to neutralize the reaction mixture to a pH of about six, to provide 88.0 g of a water-containing oily substance.

Dehydrogenation Step 90.0 g of α-methylstyrene and 0.56 g of 5% palladium/carbon catalyst (containing 50% by weight of water) were additionally added to 88.0 g of the water-containing oily substance in the reaction vessel. The atmosphere inside the reaction vessel was displaced with nitrogen gas, and the reaction vessel was heated to a temperature of 160° C. under normal pressure, followed by six hour reaction with stirring.

After the completion of the reaction, 96 g of dimethylformamide was added and mixed, and then the palladium/carbon catalyst used was removed from the resulting reaction mixture by filtration, followed by removing the solvent by distillation, thereby providing distillation residual which contained the desired product. Water was added to the distillation residual so that the desired product was crystallized out. Isopropyl alcohol was added to the resulting solid to prepare a slurry, and crystallization was again carried out. The solid was collected and dried to provide 47.4 g of 4-hydroxy-3",5"-dimethyl-4"-hydroxy-p-terphenyl as white crystals having a purity of 98.1% (high performance liquid chromatography). The yield was 81.7 mol % based on the 1-(4-hydroxyphenyl)-4,4-bis(3,5-dimethyl-4-hydroxyphenyl)cyclohexane used.

Melting point (DTA method): 231° C. Molecular weight (mass spectrometry, ($M^+$)): 291 Proton NMR (400 MHz, solvent DMSO-d, δ (ppm)): 2.25 (s, 6H), 6.88 (d, 2H, J=8.0 Hz), 7.25 (s, 2H), 7.50 (d, 2H, J=8.8 Hz), 7.58 (s, 4H), 8.80 (brs, 2H).

Example 3

Production of 4-hydroxy 3"-isopropyl-4"-hydroxy-p-terphenyl

Thermal Decomposition Step 29.3 g (0.0660 mol) of 1-(4-hydroxyphenyl)-4,4-bis(3-isopropyl-4-hydroxyphenyl)cyclohexane, 0.2 g of 48% aqueous solution of sodium hydroxide and 12.0 g of tetraethylene glycol were placed in a reaction vessel (300 mL capacity four necked flask), and the atmosphere inside the flask was displaced with nitrogen gas. The flask was evacuated to a reduced pressure of about 40 mmHg, and the thermal decomposition reaction was carried out at a temperature of about 210° C. over a period of three hours. The reaction was ceased when no more distillate was obtained. After the completion of the reaction, 50% aqueous solution of acetic acid was added to the reaction mixture to neutralize the reaction mixture to a pH of about six, to provide 33.6 g of a water-containing oily substance.

Dehydrogenation Step 31.2 g of α-methylstyrene and 0.2 g of 5% palladium/carbon catalyst (containing 50% by weight of water) were additionally added to 33.6 g of the water-containing oily substance in the reaction vessel. The atmosphere inside the reaction vessel was displaced with nitrogen gas, and the reaction vessel was heated to a temperature of 160° C. under normal pressure, followed by four hour reaction with stirring.

After the completion of the reaction, 31.2 g of dimethylformamide was added and mixed, and then the palladium/carbon catalyst used was removed from the resulting reaction mixture by filtration, followed by removing the solvent by distillation, thereby providing distillation residual which contained the desired product. Methyl isobutyl ketone and water were added to the distillation residual, the resulting water layer was separated, and the solvent was removed by distillation from the oily layer. Toluene was added to the distillation residual so that the desired product was crystallized.

The solid was collected and dried to provide 16.5 g of 4-hydroxy-3"-isopropyl-4"-hydroxy-p-terphenyl as white crystals having a purity of 99.0% (high performance liquid chromatography). The reaction yield was 81.2 mol % based on the 1-(4-hydroxyphenyl)-4,4-bis(3-isopropyl-4-hydroxyphenyl)cyclohexane used.

Melting point (DTA method): 179° C. Molecular weight (mass spectrometry, ($M^+$)): 305 Proton NMR (400 MHz, solvent DMSO-d, δ (ppm)): 1.24 (d, 6H, J=6.8 Hz), 3.25–3.29 (m, 1H), 6.87–6.90 (m, 3H), 7.33 (dd, 1H, J=8.4 Hz, J=2.0 Hz), 7.43 (d, 1H, J=2.4 Hz), 7.52 (d, 2H, J=8.8 Hz), 7.61 (s, 4H), 9.46 (brs, 1H), 9.56 (brs. 1H).

Example 4

Production of 4-hydroxy-3"-t-butyl-4"-hydroxy-p-terphenyl

Thermal Decomposition Step 25.0 g (0.0508 mol) of 1-(4-hydroxyphenyl)-4,4-bis(3-t-butyl-4-hydroxyphenyl)cyclohexane, 0.2 g of 48% aqueous solution of sodium hydroxide and 10.0 g of tetraethylene glycol were placed in a reaction vessel (300 mL capacity four necked flask), and the atmosphere inside the flask was displaced with nitrogen gas. The flask was evacuated to a reduced pressure of about 40 mmHg, and the thermal decomposition reaction was carried out at a temperature of about 210° C. over a period of three hours. The reaction was ceased when no more distillate was obtained. After the completion of the reaction, 50% aqueous solution of acetic acid was added to the reaction mixture to neutralize the reaction mixture to a pH of about six, to provide 27.3 g of a water-containing oily substance.

Dehydrogenation Step 24.5 g of α-methylstyrene and 0.2 g of 5% palladium/carbon catalyst (containing 50% by weight of water) were additionally added to 27.3 g of the water-containing oily substance in the reaction vessel. The atmosphere inside the reaction vessel was displaced by nitrogen gas, and the reaction vessel was heated to a temperature of 160° C. under normal pressure, followed by four hour reaction with stirring.

After the completion of the reaction, 50 g of dimethylformamide was added and mixed, and then the palladium/carbon catalyst was removed from the resulting reaction mixture by filtration, followed by removing the solvent by distillation, thereby providing distillation residual which contained the desired product. Methyl isopropyl ketone and water were added to the distillation residual, the resulting water layer was separated, and the solvent was removed by distillation from the oily layer. A mixture of toluene and cyclohexane was added to the distillation residual so that the desired product was crystallized. The solid was collected and dried to provide 7.7 g of 4-hydroxy-3"-t-butyl-p-terphenyl as white crystals having a purity of 97.1% (high performance liquid chromatography). The yield was 46.5 mol % based on the 1-(4-hydroxyphenyl)-4,4-bis(3-t-butyl-4-hydroxyphenyl)cyclohexane used.

Melting point (DTA method): 180.5° C. Molecular weight (mass spectrometry, (M⁻)): 317 Proton NMR (400 MHz, solvent DMSO-d, δ (ppm)): 1.42 (s, 9H), 6.89 (t, 3H, J=8.4 Hz), 7.34 (dd, 1H, J=8.4 Hz, 2.1 Hz), 7.44 (d, 1H, J=2.1 Hz), 7.52 (d, 2H, J=8.4 Hz), 7.61 (s, 4H), 9.52 (s, 1H), 9.57 (s, 1H).

Example D

Production of 4,4"-dihydroxy-p-terphenyls other than those produced in Example C Example 1

Production of 4,4"-dihydroxy-p-terphenyl

Thermal Decomposition Step 76.0 g (0.211 mol) of 1-(4-hydroxyphenyl)-4,4-bis(4-hydroxyphenyl)cyclohexane, 0.6 g of 48% aqueous solution of sodium hydroxide and 63.4 g of tetraethylene glycol were placed in a reaction vessel (200 mL capacity four necked flask), and the atmosphere inside the flask was displaced with nitrogen gas. The flask was evacuated to a reduced pressure of 100–150 mmHg, and the thermal decomposition reaction was carried out at a temperature of about 210° C. over a period of three hours. The reaction was ceased when no more distillate was obtained. After the completion of the reaction, 50% aqueous solution of acetic acid was added to the reaction mixture to neutralize the reaction mixture to a pH of about six, to provide a water-containing oily substance.

Dehydrogenation Step 49.8 g (twice in mols as much as the theoretical yield of 4,4"-hydroxyphenyl-p-cyclohexene-1) of α-methylstyrene and 5.8 g of 5% palladium/carbon catalyst (containing 50% by weight of water) were additionally added to 119 g of the water-containing oily substance in the reaction vessel. The atmosphere inside the reaction vessel was displaced by nitrogen gas, and the reaction vessel was heated to a temperature of 163° C. under normal pressure, followed by three hour reaction with stirring.

After the completion of the reaction, 1400 g of dimethylformamide was added and mixed, and then the palladium/carbon catalyst used was removed from the resulting reaction mixture by filtration, followed by removing the solvent by distillation, thereby providing distillation residual which contained the desired product. Methanol was added to the distillation residual so that the desired product was crystallized. The solid was collected and dried to provide 41.7 g of 4,4"-dihydroxy-p-terphenyl as white crystals having a purity of 98.8% (high performance liquid chromatography). The yield was 74.5 mol % based on the 1-(4-hydroxyphenyl)-4,4-bis(4-hydroxyphenyl)cyclohexane used.

Example 2

Production of 4-hydroxy-3"-methyl-4"-hydroxy-p-terphenyl

Production Step of 1-(4-hydroxyphenyl)-4,4-bis(3-methyl-4-hydroxyphenyl)cyclohexane 136 g (eight times in mols as much as the amount of 4-(4'-hydroxyphenyl)cyclohexane hereinafter mentioned) of o-cresol, 53.9 g of concentrated hydrochloric acid, 0.3 g of octylmercaptan and 27.2 g of methanol were placed in a reaction vessel (500 mL capacity four necked flask). After the resulting mixture were stirred at a temperature of 40° C., 29.0 g of powder of 4-(4'-hydroxyphenyl)-cyclohexane was added to the mixture over two hours, and the mixture was stirred for another four hours at a temperature of 40° C. The reaction selectivity was found to be 98% (high performance liquid chromatography).

After the completion of the reaction, 135 g of 16% aqueous solution of sodium hydroxide was added to neutralize the resulting reaction mixture, and then the reaction mixture was adjusted to a pH of 6 by adding thereto several drops of 75% phosphoric acid. Thereafter 100 g of methyl isobutyl ketone was added to the reaction mixture, the resulting water layer was separated, 50 g of water was added to the resulting oil layer, and the oil layer was separated from the water layer. The methanol and methyl isobutyl ketone were removed from the oil layer by distillation, thereby providing 244 g of reddish brown liquid residual.

Thermal Decomposition Step 0.60 g of 48% aqueous solution of sodium hydroxide and 18 g of tetraethylene glycol were added to 244 g of the liquid residual. The mixture was heated for three hours at a temperature of 182% under a reduced pressure of 40 mmHg while distilling the o-cresol to carry out thermal decomposition of the 1-(4-hydroxyphenyl)-4,4-bis(3-methyl-4-hydroxyphenyl)cyclohexane, resulting in provision of 63.4 g of reddish brown oily substance as residual. The reaction selectivity was found to be 91% (high performance liquid chromatography). 1.0 g of 50% aqueous solution acetic acid was added to the reddish brown oily substance to neutralize the substance, followed by stirring at a temperature of 90° C. for 20 minutes, thereby providing 64 g of creamy slurry.

Dehydrogenation Step 72 g of α-methylstyrene and 4.2 g of 5% palladium/carbon catalyst (containing 50% by weight of water) were added to the creamy slurry and, while refluxing, the dehydrogenation reaction was carried out for three hours at a temperature of 165° C. under normal pressure. The reaction selectivity was found to be 89% (high performance liquid chromatography).

After the resulting reaction mixture was cooled to room temperature, 60 g of dimethylformamide was added to the reaction mixture to dissolve the reaction mixture therein, and the catalyst used was removed by filtration from the reaction mixture. Thereafter the obtained filtrate was distilled to remove the dimethylformamide therefrom to provide 98 g of residual. Methanol was added to the residual and heated to a temperature of 60° C. to dissolve the residual therein. Water was then added to the resulting solution so that the desired product was crystallized. The solid was collected by filtration at normal temperature and dried to provide 35.7 g of 4,4"-dihydroxy-3"-methyl-p-terphenyl having a purity of 99.1%. The reaction yield was found to be 84 mol % based on the 4-(4'-hydroxyphenyl)cyclohexane used.

What is claimed is:

1. A diphenol represented by the general formula (I)

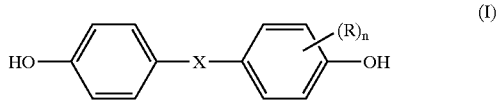
(I)

wherein X is a divalent cyclic hydrocarbon group selected from 1-cyclohexene-1,4-ylene group, 1,4-cyclohexylene group and p-phenylene group, R is an alkyl group of 1–4 carbon atoms, n is 0 or an integer of 1–3 when X is 1-cyclohexene-1,4-ylene group and an integer of 1–3 when X is 1,4-cyclohexylene group or p-phenylene group.

2. A process for production of 4,4''-dihydroxy-p-terphenyl represented by the general formula (Ic')

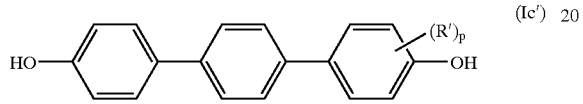
(Ic')

wherein R' is independently alkyl, alkoxyl or haloalkoxyl group each of 1–12 carbon atoms, cycloalkyl, cycloalkoxyl or halocyoloalkoxyl group each of five or six carbon atoms, phenyl or hydroxyl group, p is 0 or an integer of 1–3, which comprises thermally decomposing a hydroxyphenyl substituted cyclohexylidene bisphenol represented by the general formula (II')

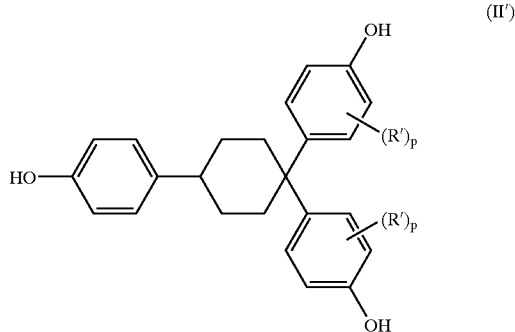
(II')

wherein R' and p are the same as above mentioned, and then subjecting the resulting reaction mixture to dehydrogenation.

3. A process for production of 4,4''-dihydroxy-p-terphenyl according to claim 2 wherein 4-(4-hydroxyphenyl) cyclohexanone is reacted with a substituted phenol represented by the general formula (III')

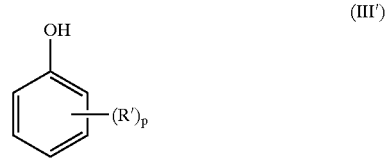
(III')

wherein R' is independently alkyl, alkoxyl or haloalkoxyl group each of 1–12 carbon atoms, cycloalkyl, cycloalkoxyl or halocycloalkoxyl group each of five or six carbon atoms, phenyl or hydroxyl group and p is 0 or an integer of 1–3, in the presence of an acid catalyst, to generate a hydroxyphenyl substituted cyclohexylidene bisphenol represented by the general formula (II')

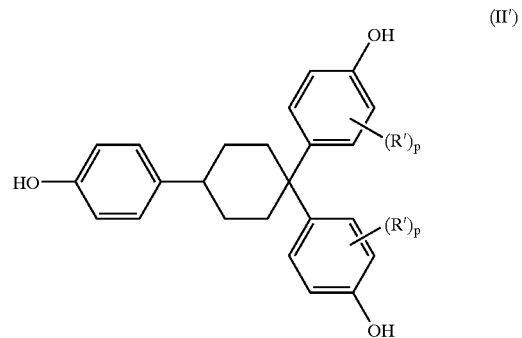
(II')

wherein R' and p are the same as above, the hydroxyphenyl substituted cyclohexylidene bisphenol is thermally decomposed, and the resulting reaction mixture is subjected to dehydrogenation.

4. A trans-isomer of the diphenol according to claim 1.

5. A cis-isomer of the diphenol according to claim 1.

* * * * *